(12) United States Patent
Hart

(10) Patent No.: US 8,618,262 B2
(45) Date of Patent: Dec. 31, 2013

(54) MONOCLONAL ANTIBODIES AGAINST DENDRITIC CELL RECEPTOR

(76) Inventor: Derek N. Hart, Christchurch (NZ)

(*) Notice: Subject to any disclaimer, the term of this patent is extended or adjusted under 35 U.S.C. 154(b) by 0 days.

(21) Appl. No.: 12/591,412

(22) Filed: Nov. 18, 2009

(65) Prior Publication Data

US 2010/0303818 A1    Dec. 2, 2010

Related U.S. Application Data

(60) Continuation of application No. 11/068,882, filed on Mar. 2, 2005, now abandoned, which is a division of application No. 10/141,956, filed on May 10, 2002, now abandoned, which is a division of application No. 09/194,612, filed as application No. PCT/NZ97/00068 on May 19, 1997, now Pat. No. 6,432,666.

(30) Foreign Application Priority Data

May 19, 1996 (NZ) ........................................ 286692

(51) Int. Cl.
*C07K 16/18* (2006.01)
(52) U.S. Cl.
USPC ................................. 530/388.1; 530/387.1
(58) Field of Classification Search
None
See application file for complete search history.

(56) References Cited

U.S. PATENT DOCUMENTS

2004/0258688 A1    12/2004    Hawiger et al. ............ 424/144.1

FOREIGN PATENT DOCUMENTS

| AU | A 49702/96 | 8/1996 |
| WO | 96/23882 | 8/1996 |

OTHER PUBLICATIONS

Swiggard et al, "DEC-205, a 205-kDa Protein Abundant . . . ," Cellular Immunology, vol. 165, pp. 302-311 (1995).

Cellular Immunology (1195) vol. 165, pp. 302-311 by Swiggard WJ et al. "DEC-205, a 205-kDa protein abundant on mouse dendritic cells and thymic epithelium that is detected by the monoclonal antibody NLDC-145; Purification, characterisation and N-terminal amino acid sequence" See the entire document.
Jiang et al; The receptor DEC-205 expressed by dendritic cells and thymic epithelial cells is involved in antigen processing; *Nature*, vol. 375; pp. 151-155, May 11, 1995.
Supplementary Partial European Search Report; European Application No. 97 92 3357, dated Dec. 12, 2000 (3 pgs).
Jiang, Wanping, et al; "The receptor DEC-205 expressed by dendritic cells and thymic epithelial cells is involved in antigen processing"; *Letters to Nature;* vol. 375, pp. 151-155 (1995) (XP000571400).
Kato, et al; "cDNA cloning of human DEC-205, a putative antigen-uptake receptor on dendritic cells"; *Immunogenetics*, vol. 47, pp. 442-450 (1998) (XP000943324).
Steinman, R.M., "The Dendritic Cell System of Antigen Presenting Cells"; *Experimental Hematology;* vol. 23, No. 8, pp. 793 (1995) (XP000571299).
Kato, M., et al; "Hodgkin's Lymphoma Cell Lines Express a Fusion Protein Encoded by Intergenically Spliced mRNA for the Multilectin Receptor DEC-205 (CD205) and a Novel C-type lectin Receptor DCL-1"; *The Journal of Biological Chemistry;* vol. 278, No. 38, pp. 34035-34041 (2003).
Breel, M., et al; Murine hybride cell lines expressing the NLDC-145 dendritic cell detriminant; *Immunobiology,* 178(3), pp. 167-176 (1988).
Swiggard, W.J., et al; "DEC-205, a 205-kDa Protein Abundant on Mouse Dendritic Cells and Thymic Epithelium That Is Detected by the Monoclonal Antibody NLDC-145: Purification, Characterization, and N-Terminal Amino Acid Sequence"; *Cellular Immunology;* vol. 165, pp. 302-311 (1996).
Inaba, K., et al; "Tissue Distribution of the DEC-205 Protein That Is Detected by the Monoclonal Antibody NLDC-145"; *Cellular Immunology;* vol. 163, pp. 148-156 (1995).

*Primary Examiner* — Ruixiang Li
(74) *Attorney, Agent, or Firm* — Nixon & Vanderhye

(57) ABSTRACT

The invention provides isolated human DEC-205, its extracellular domain and functionally equivalent fragments thereof. Also provided are polynucleotides encoding same and vectors which include such polynucleotides. Further provided are methods of recombinantly producing human DEC-205, an extracellular domain thereof or a functionally equivalent fragment, and ligands that bind to human DEC-205 or a fragment thereof. Also provided are constructs for use in prophylaxis or therapy comprising such a ligand, human DEC-205 or an extracellular domain thereof coupled to a toxin or to an antigen capable of inducing a protective immune response in a patient.

2 Claims, 15 Drawing Sheets

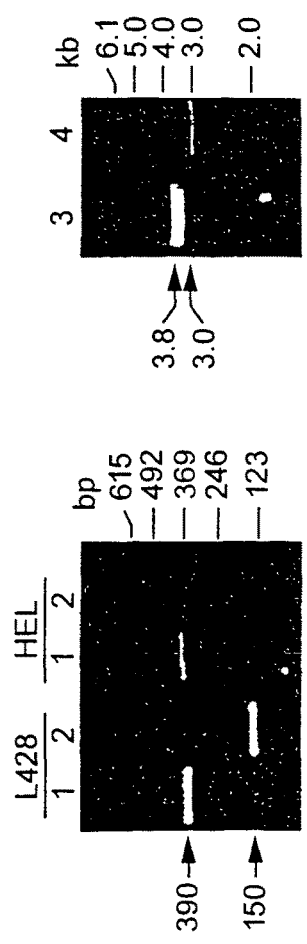
Figure 2B
Figure 2C
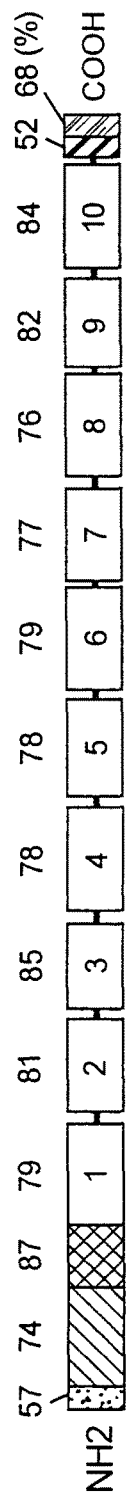
Figure 3B

```
                      Signal peptide                              Cysteine-rich domain
human    1  MRTGWAKP SPPGQAPHAALLYLRSRQ       27  ALMPRTRDPFTIVHGATQKCIKFVYGATVADDCDETEQKLWRWSQHRLFHLHSQKCLGLDITKSVELRMYS
mouse    1  MRTQRV  T PQLAAGLLLLRSFQLVEP      28  SHSSGRDPFTIVHETAQKIQPLSDWVAQDCSQTNRMLMRWVSQHRLFHLHSQKCLQLDITKATDNLRMFS Fibronectin type II domain
human        CDSSAKLRWKCEHHBLYGAARYMLALKDGHGTAISSASDVWKGGSESLCDQPYHEI     158 ITRDONSYGRPCLFPFLIDGTHHEDCILDEDHSGPHCATTLNYEY
mouse        CDSTVMLRWKCHHSLYTAAQYRLALKDGTAVANTHTSDVWKKGGSHENLCAQPYHEI     158 ITRDGNHYGRPCHFPFLIGKTWYEDCIHDEDHSGWCATTLSYEY CRD-1
human        DRKWGICLKP         ENG  216  CHEDNWEKHEOFQSCYQFNTQTALSHKEAYVSCCHHQGADLLSINSAALILTYLKKSGIAKIFMIGLNQLYBARGWNSDHKPLNFL
mouse        DQKWGICLLP         ESG  216  CEGRMELHEQIGSCYQFNHQEILSWKEAYVSCQNQGADLLSIHBALABLAYITOKHDFARLVHLGLHQLYSARGMFWSDFTPLKKTL CRD-2
human        NMDPDRPSAPTIGGSSCARMDAESGLMQSFSCEAQLPYVCRK       361  CDAGNLPHRMFCYLLVESNSWDKAHLKCRAFSSDLI
mouse        NMDPGTPVAPVIGASBCARMDTESGLMQSVSCKSQQPYVCKK       361  CHVGMLPNHMFCYLLANESSBWDAAHLKCRAFGADLI human        SIHSLADVETVVTKLHNEDIKRKVHIGLKINIPTLFQNSDGTNVTLTTHDESIPNVF YNKTRPNCVSYLGELGMHKVQSCHERLKFVCRK    GEKLNDASSDKM
mouse        SHESLADVEVVTKLHNQDVAKHIHTGLRKTHSPALFQNSDGTNVTTLATVNNENEPSVFFAKIPNCVSYLGKLGQHKVQSCHKGLRYVCKK    GHITKDASSDRL CRD-3
human        CPPDIGWKRHGETCYKIISDEVPFGTNCHLTITSRFEQIYLNDLMKKYDSLRKYFHTGLRDVDSCOBYNHATVGGRRAVTTSNWHFLEPASPGGCVAHSTGKSV
mouse        CPPDEGWKRHGITCYKIIYAKELAPGTNCNLITITSRFEQETLAYOSKNYCKSLRKYFHTGLRDPDSRGEYSHAVAQQVKQAVTPSNMHFLAPASPGGCVAHSTQKTL CRD-4
human        QKWHVKDCRSFKKLSICKK        MSGRLQPEEASPKPDDP     643  CPEGMQSTPASLSCYKVTHAMRIVRFRWERARFCQALGAHLSSTSHVDEIKETLRYLTDQ
mouse        QKWHVKRCRSFRALSICKK        VSERQEREIAAPKPDDP     643  CPEGMHTFPSBLSCYKVTHIERIVRGRWELARFCQALGAHLPFSRREBIKDSFVBLLKDQ human        FSGQHWHIWIGLKKRSPDLQQSHQHSDRTFVSTIIHPHEFQQDYDIRDCAAVKVTHRAPNRRGMHTTDDREFIYLAPPACDTKLKFVCQI    PKGRTPKTPLWYSPDRAG
mouse        FSGQRWHIFIGLNKRBPDLQQSHQNSDRTFVSAVHREFHQQDFDIRDCAAIKVLDVTPRRVHKLYEKDYAYHKPFACDAKLENVCQI       PKGSTPQMPDWYNFERTG CRD-5
human    811 IHGPPLLILGSEYNFVADLIHLYTRAVLYCASKHSFLATITSFVGLKA=KHKIAHISGDGQKNRIRISEMPIDDHFTYSRYP .MERFPVTFGERCLYMSAKTWLID
mouse    811 IHGPPVIIEGSEYWFVADPHLNYERAVLYCASRHSFLATISFTQLKAIKHKLAHISQREQRKMHVKTSENPIDRYTLGSRRRLMEHFPMTFQDECLHHSARTWLVD
```

Figure 3A-1

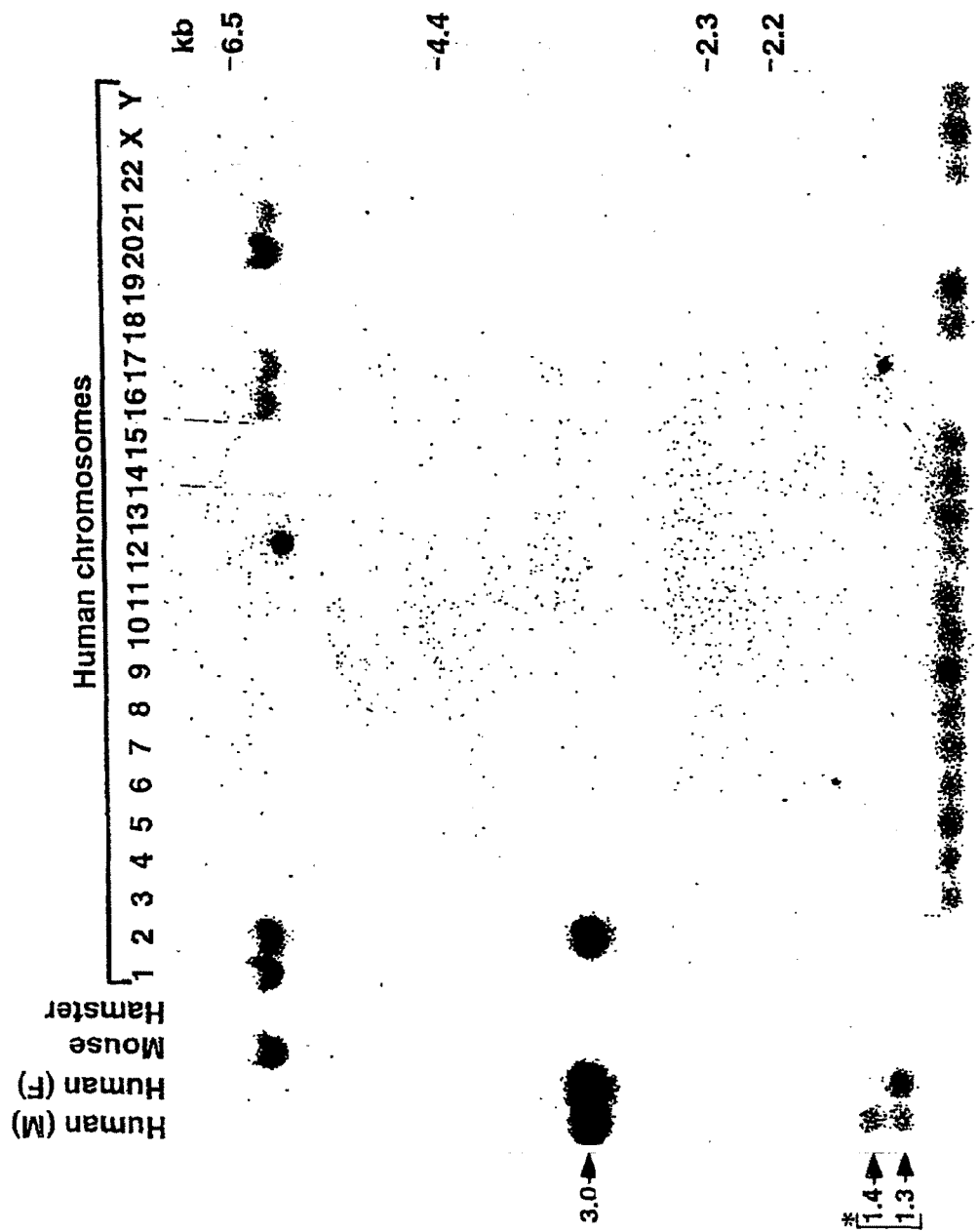

DEC-205 DNA sequence (coding region only)

```
   1 ATGAGGACAG GCTGGGCGCA CCCCTCGCCG CCCGGCGGGG CTCCTCATGC
  51 TGCTCTTCTG GTTCTTCGAT CTCGCGGAGC CCTCTGGCCG CGCACTAATG
 101 ACCCCTTCAC CATCGTCCAT GGAAATACGG GCAAGTGCAT CAAGCCAGTG
 151 TATGGCTGGA TAGTAGCAGA CGACTGTGAT GAAACTGAGG ACAAGTTATG
 201 GAAGTGGGTG TCCCAGCATC GGCTCTTTCA TTTGCACTCC CAAAAGTGCC
 251 TTGGCCTCGA TATTACCAAA TCGGTAAATG AGCTGAGAAT GTTCAGCTGT
 301 GACTCCAGTG CCATGCTGTG GTGGAAATGT GAGCACCACT CTCTGTACGG
 351 AGCTGCCCGG TACTGGCTGG CTCTGAAGGA TGGACATGGC ACAGCAATCT
 401 CAAATGCATC TGATGTCTGG AAGAAAGGAG GCTCAGAGGA AAGCCTTTGT
 451 GACCAGCCTT ATCATGAGAT CTATACCAGA GATGGGAACT CTTATGGGAG
 501 ACCTTGTGAA TTTCCATTCT TAATTGATGG GACCTGGCAT CATGATTGCA
 551 TTCTTGATGA AGATCATAGT GGGCCATGGT GTGCCACCAC CTTAAATTAT
 601 GAATATGACC GAAAGTGGGG CATCTGCTTA AAGCCTGAAA ACGGTTGTGA
 651 AGATAATTGG GAAAAGAACG AGCAGTTTGG AAGTTGCTAC CAATTTAATA
 701 CTCAGACGGC TCTTTCTTGG AAAGAAGCTT ATGTTTCATG TCAGAATCAA
 751 GGAGCTGATT TACTGAGCAT CAACAGTGCT GCTGAATTAA CTTACCTTAA
 801 AGAAAAAGAA GGCATTGCTA AGATTTTCTG GATTGGTTTA AATCAGCTAT
 851 ACTCTGCTAG AGGCTGGGAA TGGTCAGACC ACAAACCATT AAACTTTCTC
 901 AACTGGGATC CAGACAGGCC CAGTGCACCT ACTATAGGTG GCTCCAGCTG
 951 TGCAAGAATG GATGCTGAGT CTGGTCTGTG GCAGAGCTTT TCCTGTGAAG
1001 CTCAACTGCC CTATGTCTGC AGGAAACCAT TAAATAATAC AGTGGAGTTA
1051 ACAGATGTCT GGACATACTC AGATACCCGC TGTGATGCAG GCTGGCTGCC
1101 AAATAATGGA TTTTGCTATC TGCTGGTAAA TGAAAGTAAT TCCTGGGATA
1151 AGGCACATGC GAAATGCAAA GCCTTCAGTA GTGACCTAAT CAGCATTCAT
1201 TCTCTAGCAG ATGTGGAGGT GGTTGTCACA AAACTCCATA ATGAGGATAT
1251 CAAAGAAGAA GTGTGGATAG GCCTTAAGAA CATAAACATA CCAACTTTAT
```

Figure 10A

1301 TTCAGTGGTC AGATGGTACT GAAGTTACTC TAACATATTG GGATGAGAAT

1351 GAGCCAAATG TTCCCTACAA TAAGACGCCC AACTGTGTTT CCTACTTAGG

1401 AGAGCTAGGT CAGTGGAAAG TCCAATCATG TGAGGAGAAA CTAAAATATG

1451 TATGCAAGAG AAAGGGAGAA AAACTGAATG ACGCAAGTTC TGATAAGATG

1501 TGTCCTCCAG ATGAGGGCTG GAAGAGACAT GGAGAAACCT GTTACAAGAT

1551 TTATGAGGAT GAGGTCCCTT TTGGAACAAA CTGCAATCTG ACTATCACTA

1601 GCAGATTTGA GCAAGAATAC CTAAATGATT TGATGAAAAA GTATGATAAA

1651 TCTCTAAGAA AATACTTCTG GACTGGCCTG AGAGATGTAG ATTCTTGTGG

1701 AGAGTATAAC TGGGCAACTG TTGGTGGAAG AAGGCGGGCT GTAACCTTTT

1751 CCAACTGGAA TTTTCTTGAG CCAGCTTCCC CGGGCGGCTG CGTGGCTATG

1801 TCTACTGGAA AGTCTGTTGG AAAGTGGGAG GTGAAGGACT GCAGAAGCTT

1851 CAAAGCACTT TCAATTTGCA AGAAAATGAG TGGACCCCTT GGGCCTGAAG

1901 AAGCATCCCC TAAGCCTGAT GACCCTGTC CTGAAGGCTG GCAGAGTTTC

1951 CCCGCAAGTC TTTCTTGTTA TAAGGTATTC CATGCAGAAA GAATTGTAAG

2001 AAAGAGGAAC TGGGAAGAAG CTGAACGATT CTGCCAAGCC CTTGGAGCAC

2051 ACCTTTCTAG CTTCAGCCAT GTGGATGAAA TAAAGGAATT TCTTCACTTT

2101 TTAACGGACC AGTTCAGTGG CCAGCATTGG CTGTGGATTG GTTTGAATAA

2151 AAGGAGCCCA GATTTACAAG GATCCTGGCA ATGGAGTGAT CGTACACCAG

2201 TGTCTACTAT TATCATGCCA AATGAGTTTC AGCAGGATTA TGACATCAGA

2251 GACTGTGCTG CTGTCAAGGT ATTTCATAGG CCATGGCGAA GAGGCTGGCA

2301 TTTCTATGAT GATAGAGAAT TTATTTATTT GAGGCCTTTT GCTTGTGATA

2351 CAAAACTTGA ATGGGTGTGC CAAATTCCAA AAGGCCGTAC TCCAAAAACA

2401 CCAGACTGGT ACAATCCAGA CCGTGCTGGA ATTCATGGAC CTCCACTTAT

2451 AATTGAAGGA AGTGAATATT GGTTTGTTGC TGATCTTCAC CTAAACTATG

2501 AAGAAGCCGT CCTGTACTGT GCCAGCAATC ACAGCTTTCT TGCGACTATA

2551 ACATCTTTTG TGGGACTAAA AGCCATCAAA AACAAAATAG CAAATATATC

2601 TGGTGATGGA CAGAAGTGGT GGATAAGAAT TAGCGAGTGG CCAATAGATG

Figure 10B

```
2651 ATCATTTTAC ATACTCACGA TATCCATGGC ACCGCTTTCC TGTGACATTT
2701 GGAGAGGAAT GCTTGTACAT GTCTGCCAAG ACTTGGCTTA TCGACTTAGG
2751 TAAACCAACA GACTGTAGTA CCAAGTTGCC CTTCATCTGT GAAAAATATA
2801 ATGTTTCTTC GTTAGAGAAA TACAGCCCAG ATTCTGCAGC TAAAGTGCAA
2851 TGTTCTGAGC AATGGATTCC TTTTCAGAAT AAGTGTTTTC TAAAGATCAA
2901 ACCCGTGTCT CTCACATTTT CTCAAGCAAG CGATACCTGT CACTCCTATG
2951 GTGGCACCCT TCCTTCAGTG TTGAGCCAGA TTGAACAAGA CTTTATTACA
3001 TCCTTGCTTC CGGATATGGA AGCTACTTTA TGGATTGGTT TGCGCTGGAC
3051 TGCCTATGAA AAGATAAACA AATGGACAGA TAACAGAGAG CTGACGTACA
3101 GTAACTTTCA CCCATTATTG GTTAGTGGGA GGCTGAGAAT ACCAGAAAAT
3151 TTTTTTGAGG AAGAGTCTCG CTACCACTGT GCCCTAATAC TCAACCTCCA
3201 AAAATCACCG TTTACTGGGA CGTGGAATTT TACATCCTGC AGTGAACGCC
3251 ACTTTGTGTC TCTCTGTCAG AAATATTCAG AAGTTAAAAG CAGACAGACG
3301 TTGCAGAATG CTTCAGAAAC TGTAAAGTAT CTAAATAATC TGTACAAAAT
3351 AATCCCAAAG ACTCTGACTT GGCACAGTGC TAAAAGGGAG TGTCTGAAAA
3401 GTAACATGCA GCTGGTGAGC ATCACGGACC CTTACCAGCA GGCATTCCTC
3451 AGTGTGCAGG CGCTCCTTCA CAACTCTTCC TTATGGATCG GACTCTTCAG
3501 TCAAGATGAT GAACTCAACT TTGGTTGGTC AGATGGGAAA CGTCTTCATT
3551 TTAGTCGCTG GGCTGAAACT AATGGGCAAC TCGAAGACTG TGTAGTATTA
3601 GACACTGATG GATTCTGGAA AACAGTTGAT TGCAATGACA ATCAACCAGG
3651 TGCTATTTGC TACTATTCAG GAAATGAGAC TGAAAAAGAG GTCAAACCAG
3701 TTGACAGTGT TAAATGTCCA TCTCCTGTTC TAAATACTCC GTGGATACCA
3751 TTTCAGAACT GTTGCTACAA TTTCATAATA ACAAAGAATA GGCATATGGC
3801 AACAACACAG GATGAAGTTC ATACTAAATG CCAGAAACTG AATCCAAAAT
3851 CACATATTCT GAGTATTCGA GATGAAAAGG AGAATAACTT TGTTCTTGAG
3901 CAACTGCTGT ACTTCAATTA TATGGCTTCA TGGGTCATGT TAGGAATAAC
3951 TTATAGAAAT AATTCTCTTA TGTGGTTTGA TAAGACCCCA CTGTCATATA
```

Figure 10C

```
4001 CACATTGGAG AGCAGGAAGA CCAACTATAA AAAATGAGAA GTTTTTGGCT
4051 GGTTTAAGTA CTGACGGCTT CTGGGATATT CAAACCTTTA AAGTTATTGA
4101 AGAAGCAGTT TATTTTCACC AGCACAGCAT TCTTGCTTGT AAAATTGAAA
4151 TGGTTGACTA CAAAGAAGAA CATAATACTA CACTGCCACA GTTTATGCCA
4201 TATGAAGATG GTATTTACAG TGTTATTCAA AAAAAGGTAA CATGGTATGA
4251 AGCATTAAAC ATGTGTTCTC AAAGTGGAGG TCACTTGGCA AGCGTTCACA
4301 ACCAAAATGG CCAGCTCTTT CTGGAAGATA TTGTAAAACG TGATGGATTT
4351 CCACTATGGG TTGGGCTCTC AAGTCATGAT GGAAGTGAAT CAAGTTTTGA
4401 ATGGTCTGAT GGTAGTACAT TGACTATAT CCCATGGAAA GGCCAAACAT
4451 CTCCTGGAAA TTGTGTTCTC TTGGATCCAA AAGGAACTTG GAAACATGAA
4501 AAATGCAACT CTGTTAAGGA TGGTGCTATT TGTTATAAAC CTACAAAATC
4551 TAAAAAGCTG TCCCGTCTTA CATATTCATC AAGATGTCCA GCAGCAAAAG
4601 AGAATGGGTC ACGGTGGATC CAGTACAAGG GTCACTGTTA CAAGTCTGAT
4651 CAGGCATTGC ACAGTTTTTC AGAGGCCAAA AAATTGTGTT CAAAACATGA
4701 TCACTCTGCA ACTATCGTTT CCATAAAAGA TGAAGATGAG AATAAATTTG
4751 TGAGCAGACT GATGAGGGAA AATAATAACA TTACCATGAG AGTTTGGCTT
4801 GGATTATCTC AACATTCTGT TGACCAGTCT TGGAGTTGGT TAGATGGATC
4851 AGAAGTGACA TTTGTCAAAT GGGAAAATAA AAGTAAGAGT GGTGTTGGAA
4901 GATGTAGCAT GTTGATAGCT TCAAATGAAA CTTGGAAAAA AGTTGAATGT
4951 GAACATGGTT TTGGAAGAGT TGTCTGCAAA GTGCCTCTGG GCCCTGATTA
5001 CACAGCAATA GCTATCATAG TTGCCACACT AAGTATCTTA GTTCTCATGG
5051 GCGGACTGAT TTGGTTCCTC TTCCAAAGGC ACCGTTTGCA CCTGGCGGGT
5101 TTCTCATCAG TTCGATATGC ACAAGGAGTG AATGAAGATG AGATTATGCT
5151 TCCTTCTTTC CATGAC
```

Figure 10D

DEC-205 protein sequence

```
   1 MRTGWAHPSP PGGAPHAALL VLRSRGALWP RTNDPFTIVH GNTGKCIKPV
  51 YGWIVADDCD ETEDKLWKWV SQHRLFHLHS QKCLGLDITK SVNELRMFSC
 101 DSSAMLWWKC EHHSLYGAAR YWLALKDGHG TAISNASDVW KKGGSEESLC
 151 DQPYHEIYTR DGNSYGRPCE FPFLIDGTWH HDCILDEDHS GPWCATTLNY
 201 EYDRKWGICL KPENGCEDNW EKNEQFGSCY QFNTQTALSW KEAYVSCQNQ
 251 GADLLSINSA AELTYLKEKE GIAKIFWIGL NQLYSARGWE WSDHKPLNFL
 301 NWDPDRPSAP TIGGSSCARM DAESGLWQSF SCEAQLPYVC RKPLNNTVEL
 351 TDVWTYSDTR CDAGWLPNNG FCYLLVNESN SWDKAHAKCK AFSSDLISIH
 401 SLADVEVVVT KLHNEDIKEE VWIGLKNINI PTLFQWSDGT EVTLTYWDEN
 451 EPNVPYNKTP NCVSYLGELG QWKVQSCEEK LKYVCKRKGE KLNDASSDKM
 501 CPPDEGWKRH GETCYKIYED EVPFGTNCNL TITSRFEQEY LNDLMKKYDK
 551 SLRKYFWTGL RDVDSCGEYN WATVGGRRRA VTFSNWNFLE PASPGGCVAM
 601 STGKSVGKWE VKDCRSFKAL SICKKMSGPL GPEEASPKPD DPCPEGWQSF
 651 PASLSCYKVF HAERIVRKRN WEEAERFCQA LGAHLSSFSH VDEIKEFLHF
 701 LTDQFSGQHW LWIGLNKRSP DLQGSWQWSD RTPVSTIIMP NEFQQDYDIR
 751 DCAAVKVFHR PWRRGWHFYD DREFIYLRPF ACDTKLEWVC QIPKGRTPKT
 801 PDWYNPDRAG IHGPPLIIEG SEYWFVADLH LNYEEAVLYC ASNHSFLATI
 851 TSFVGLKAIK NKIANISGDG QKWWIRISEW PIDDHFTYSR YPWHRFPVTF
 901 GEECLYMSAK TWLIDLGKPT DCSTKLPFIC EKYNVSSLEK YSPDSAAKVQ
 951 CSEQWIPFQN KCFLKIKPVS LTFSQASDTC HSYGGTLPSV LSQIEQDFIT
1001 SLLPDMEATL WIGLRWTAYE KINKWTDNRE LTYSNFHPLL VSGRLRIPEN
1051 FFEEESRYHC ALILNLQKSP FTGTWNFTSC SERHFVSLCQ KYSEVKSRQT
1101 LQNASETVKY LNNLYKIIPK TLTWHSAKRE CLKSNMQLVS ITDPYQQAFL
1151 SVQALLHNSS LWIGLFSQDD ELNFGWSDGK RLHFSRWAET NGQLEDCVVL
1201 DTDGFWKTVD CNDNQPGAIC YYSGNETEKE VKPVDSVKCP SPVLNTPWIP
1251 FQNCCYNFII TKNRHMATTQ DEVHTKCQKL NPKSHILSIR DEKENNFVLE
```

Figure 11A

1301 QLLYFNYMAS WVMLGITYRN NSLMWFDKTP LSYTHWRAGR PTIKNEKFLA

1351 GLSTDGFWDI QTFKVIEEAV YFHQHSILAC KIEMVDYKEE HNTTLPQFMP

1401 YEDGIYSVIQ KKVTWYEALN MCSQSGGHLA SVHNQNGQLF LEDIVKRDGF

1451 PLWVGLSSHD GSESSFEWSD GSTFDYIPWK GQTSPGNCVL LDPKGTWKHE

1501 KCNSVKDGAI CYKPTKSKKL SRLTYSSRCP AAKENGSRWI QYKGHCYKSD

1551 QALHSFSEAK KLCSKHDHSA TIVSIKDEDE NKFVSRLMRE NNNITMRVWL

1601 GLSQHSVDQS WSWLDGSEVT FVKWENKSKS GVGRCSMLIA SNETWKKVEC

1651 EHGFGRVVCK VPLGPDYTAI AIIVATLSIL VLMGGLIWFL FQRHRLHLAG

1701 FSSVRYAQGV NEDEIMLPSF HD*

Figure 11B

SEQUENCE LISTING

<160> NUMBER OF SEQ ID NOS: 36

<210> SEQ ID NO 1
<211> LENGTH: 1722
<212> TYPE: PRT
<213> ORGANISM: Homo sapiens

<400> SEQUENCE: 1

```
Met Arg Thr Gly Trp Ala His Pro Ser Pro Pro Gly Gly Ala Pro His
 1               5                  10                  15

Ala Ala Leu Leu Val Leu Arg Ser Arg Gly Ala Leu Trp Pro Arg Thr
            20                  25                  30

Asn Asp Pro Phe Thr Ile Val His Gly Asn Thr Gly Lys Cys Ile Lys
        35                  40                  45

Pro Val Tyr Gly Trp Ile Val Ala Asp Asp Cys Asp Glu Thr Glu Asp
    50                  55                  60

Lys Leu Trp Lys Trp Val Ser Gln His Arg Leu Phe His Leu His Ser
65                  70                  75                  80

Gln Lys Cys Leu Gly Leu Asp Ile Thr Lys Ser Val Asn Glu Leu Arg
                85                  90                  95

Met Phe Ser Cys Asp Ser Ser Ala Met Leu Trp Trp Lys Cys Glu His
            100                 105                 110
```

```
His Ser Leu Tyr Gly Ala Ala Arg Tyr Trp Leu Ala Leu Lys Asp Gly
        115                 120                 125
His Gly Thr Ala Ile Ser Asn Ala Ser Asp Val Trp Lys Lys Gly Gly
        130                 135                 140
Ser Glu Glu Ser Leu Cys Asp Gln Pro Tyr His Glu Ile Tyr Thr Arg
145                 150                 155                 160
Asp Gly Asn Ser Tyr Gly Arg Pro Cys Glu Phe Pro Phe Leu Ile Asp
                165                 170                 175
Gly Thr Trp His His Asp Cys Ile Leu Asp Glu Asp His Ser Gly Pro
            180                 185                 190
Trp Cys Ala Thr Thr Leu Asn Tyr Glu Tyr Asp Arg Lys Trp Gly Ile
        195                 200                 205
Cys Leu Lys Pro Glu Asn Gly Cys Glu Asp Asn Trp Glu Lys Asn Glu
210                 215                 220
Gln Phe Gly Ser Cys Tyr Gln Phe Asn Thr Gln Thr Ala Leu Ser Trp
225                 230                 235                 240
Lys Glu Ala Tyr Val Ser Cys Gln Asn Gln Gly Ala Asp Leu Leu Ser
                245                 250                 255
Ile Asn Ser Ala Ala Glu Leu Thr Tyr Leu Lys Glu Lys Glu Gly Ile
            260                 265                 270
Ala Lys Ile Phe Trp Ile Gly Leu Asn Gln Leu Tyr Ser Ala Arg Gly
        275                 280                 285
Trp Glu Trp Ser Asp His Lys Pro Leu Asn Phe Leu Asn Trp Asp Pro
290                 295                 300
Asp Arg Pro Ser Ala Pro Thr Ile Gly Gly Ser Ser Cys Ala Arg Met
305                 310                 315                 320
Asp Ala Glu Ser Gly Leu Trp Gln Ser Phe Ser Cys Glu Ala Gln Leu
                325                 330                 335
Pro Tyr Val Cys Arg Lys Pro Leu Asn Asn Thr Val Glu Leu Thr Asp
            340                 345                 350
Val Trp Thr Tyr Ser Asp Thr Arg Cys Asp Ala Gly Trp Leu Pro Asn
        355                 360                 365
Asn Gly Phe Cys Tyr Leu Leu Val Asn Glu Ser Asn Ser Trp Asp Lys
370                 375                 380
Ala His Ala Lys Cys Lys Ala Phe Ser Ser Asp Leu Ile Ser Ile His
385                 390                 395                 400
Ser Leu Ala Asp Val Glu Val Val Thr Lys Leu His Asn Glu Asp
                405                 410                 415
Ile Lys Glu Glu Val Trp Ile Gly Leu Lys Asn Ile Asn Ile Pro Thr
            420                 425                 430
Leu Phe Gln Trp Ser Asp Gly Thr Glu Val Thr Leu Thr Tyr Trp Asp
        435                 440                 445
Glu Asn Glu Pro Asn Val Pro Tyr Asn Lys Thr Pro Asn Cys Val Ser
450                 455                 460
Tyr Leu Gly Glu Leu Gly Gln Trp Lys Val Gln Ser Cys Glu Glu Lys
465                 470                 475                 480
Leu Lys Tyr Val Cys Lys Arg Lys Gly Glu Lys Leu Asn Asp Ala Ser
                485                 490                 495
Ser Asp Lys Met Cys Pro Pro Asp Glu Gly Trp Lys Arg His Gly Glu
            500                 505                 510
Thr Cys Tyr Lys Ile Tyr Glu Asp Glu Val Pro Phe Gly Thr Asn Cys
        515                 520                 525
Asn Leu Thr Ile Thr Ser Arg Phe Glu Gln Glu Tyr Leu Asn Asp Leu
530                 535                 540
```

```
Met Lys Lys Tyr Asp Lys Ser Leu Arg Lys Tyr Phe Trp Thr Gly Leu
545                 550                 555                 560

Arg Asp Val Asp Ser Cys Gly Glu Tyr Asn Trp Ala Thr Val Gly Gly
                565                 570                 575

Arg Arg Arg Ala Val Thr Phe Ser Asn Trp Asn Phe Leu Glu Pro Ala
            580                 585                 590

Ser Pro Gly Gly Cys Val Ala Met Ser Thr Gly Lys Ser Val Gly Lys
                595                 600                 605

Trp Glu Val Lys Asp Cys Arg Ser Phe Lys Ala Leu Ser Ile Cys Lys
        610                 615                 620

Lys Met Ser Gly Pro Leu Gly Pro Glu Glu Ala Ser Pro Lys Pro Asp
625                 630                 635                 640

Asp Pro Cys Pro Glu Gly Trp Gln Ser Phe Pro Ala Ser Leu Ser Cys
                645                 650                 655

Tyr Lys Val Phe His Ala Glu Arg Ile Val Arg Lys Arg Asn Trp Glu
                660                 665                 670

Glu Ala Glu Arg Phe Cys Gln Ala Leu Gly Ala His Leu Ser Ser Phe
            675                 680                 685

Ser His Val Asp Glu Ile Lys Glu Phe Leu His Phe Leu Thr Asp Gln
        690                 695                 700

Phe Ser Gly Gln His Trp Leu Trp Ile Gly Leu Asn Lys Arg Ser Pro
705                 710                 715                 720

Asp Leu Gln Gly Ser Trp Gln Trp Ser Asp Arg Thr Pro Val Ser Thr
                725                 730                 735

Ile Ile Met Pro Asn Glu Phe Gln Gln Asp Tyr Asp Ile Arg Asp Cys
                740                 745                 750

Ala Ala Val Lys Val Phe His Arg Pro Trp Arg Arg Gly Trp His Phe
            755                 760                 765

Tyr Asp Asp Arg Glu Phe Ile Tyr Leu Arg Pro Phe Ala Cys Asp Thr
        770                 775                 780

Lys Leu Glu Trp Val Cys Gln Ile Pro Lys Gly Arg Thr Pro Lys Thr
785                 790                 795                 800

Pro Asp Trp Tyr Asn Pro Asp Arg Ala Gly Ile His Gly Pro Pro Leu
                805                 810                 815

Ile Ile Glu Gly Ser Glu Tyr Trp Phe Val Ala Asp Leu His Leu Asn
                820                 825                 830

Tyr Glu Glu Ala Val Leu Tyr Cys Ala Ser Asn His Ser Phe Leu Ala
            835                 840                 845

Thr Ile Thr Ser Phe Val Gly Leu Lys Ala Ile Lys Asn Lys Ile Ala
850                 855                 860

Asn Ile Ser Gly Asp Gly Gln Lys Trp Trp Ile Arg Ile Ser Glu Trp
865                 870                 875                 880

Pro Ile Asp Asp His Phe Thr Tyr Ser Arg Tyr Pro Trp His Arg Phe
                885                 890                 895

Pro Val Thr Phe Gly Glu Glu Cys Leu Tyr Met Ser Ala Lys Thr Trp
                900                 905                 910

Leu Ile Asp Leu Gly Lys Pro Thr Asp Cys Ser Thr Lys Leu Pro Phe
            915                 920                 925

Ile Cys Glu Lys Tyr Asn Val Ser Ser Leu Glu Lys Tyr Ser Pro Asp
        930                 935                 940

Ser Ala Ala Lys Val Gln Cys Ser Glu Gln Trp Ile Pro Phe Gln Asn
945                 950                 955                 960
```

-continued

```
Lys Cys Phe Leu Lys Ile Lys Pro Val Ser Leu Thr Phe Ser Gln Ala
                965                 970                 975

Ser Asp Thr Cys His Ser Tyr Gly Gly Thr Leu Pro Ser Val Leu Ser
            980                 985                 990

Gln Ile Glu Gln Asp Phe Ile Thr Ser Leu Leu Pro Asp Met Glu Ala
        995                1000                1005

Thr Leu Trp Ile Gly Leu Arg Trp Thr Ala Tyr Glu Lys Ile Asn Lys
   1010                1015                1020

Trp Thr Asp Asn Arg Glu Leu Thr Tyr Ser Asn Phe His Pro Leu Leu
1025                1030                1035                1040

Val Ser Gly Arg Leu Arg Ile Pro Glu Asn Phe Phe Glu Glu Glu Ser
            1045                1050                1055

Arg Tyr His Cys Ala Leu Ile Leu Asn Leu Gln Lys Ser Pro Phe Thr
            1060                1065                1070

Gly Thr Trp Asn Phe Thr Ser Cys Ser Glu Arg His Phe Val Ser Leu
            1075                1080                1085

Cys Gln Lys Tyr Ser Glu Val Lys Ser Arg Gln Thr Leu Gln Asn Ala
            1090                1095                1100

Ser Glu Thr Val Lys Tyr Leu Asn Asn Leu Tyr Lys Ile Ile Pro Lys
1105                1110                1115                1120

Thr Leu Thr Trp His Ser Ala Lys Arg Glu Cys Leu Lys Ser Asn Met
            1125                1130                1135

Gln Leu Val Ser Ile Thr Asp Pro Tyr Gln Gln Ala Phe Leu Ser Val
            1140                1145                1150

Gln Ala Leu Leu His Asn Ser Ser Leu Trp Ile Gly Leu Phe Ser Gln
            1155                1160                1165

Asp Asp Glu Leu Asn Phe Gly Trp Ser Asp Gly Lys Arg Leu His Phe
            1170                1175                1180

Ser Arg Trp Ala Glu Thr Asn Gly Gln Leu Glu Asp Cys Val Val Leu
1185                1190                1195                1200

Asp Thr Asp Gly Phe Trp Lys Thr Val Asp Cys Asn Asp Asn Gln Pro
            1205                1210                1215

Gly Ala Ile Cys Tyr Tyr Ser Gly Asn Glu Thr Glu Lys Glu Val Lys
            1220                1225                1230

Pro Val Asp Ser Val Lys Cys Pro Ser Pro Val Leu Asn Thr Pro Trp
            1235                1240                1245

Ile Pro Phe Gln Asn Cys Cys Tyr Asn Phe Ile Ile Thr Lys Asn Arg
            1250                1255                1260

His Met Ala Thr Thr Gln Asp Glu Val His Thr Lys Cys Gln Lys Leu
1265                1270                1275                1280

Asn Pro Lys Ser His Ile Leu Ser Ile Arg Asp Glu Lys Glu Asn Asn
            1285                1290                1295

Phe Val Leu Glu Gln Leu Leu Tyr Phe Asn Tyr Met Ala Ser Trp Val
        1300                1305                1310

Met Leu Gly Ile Thr Tyr Arg Asn Asn Ser Leu Met Trp Phe Asp Lys
        1315                1320                1325

Thr Pro Leu Ser Tyr Thr His Trp Arg Ala Gly Arg Pro Thr Ile Lys
   1330                1335                1340

Asn Glu Lys Phe Leu Ala Gly Leu Ser Thr Asp Gly Phe Trp Asp Ile
1345                1350                1355                1360

Gln Thr Phe Lys Val Ile Glu Glu Ala Val Tyr Phe His Gln His Ser
            1365                1370                1375

Ile Leu Ala Cys Lys Ile Glu Met Val Asp Tyr Lys Glu Glu His Asn
            1380                1385                1390
```

Thr Thr Leu Pro Gln Phe Met Pro Tyr Glu Asp Gly Ile Tyr Ser Val
    1395                1400                1405

Ile Gln Lys Lys Val Thr Trp Tyr Glu Ala Leu Asn Met Cys Ser Gln
    1410                1415                1420

Ser Gly Gly His Leu Ala Ser Val His Asn Gln Asn Gly Gln Leu Phe
1425                1430                1435                1440

Leu Glu Asp Ile Val Lys Arg Asp Gly Phe Pro Leu Trp Val Gly Leu
    1445                1450                1455

Ser Ser His Asp Gly Ser Glu Ser Ser Phe Glu Trp Ser Asp Gly Ser
        1460                1465                1470

Thr Phe Asp Tyr Ile Pro Trp Lys Gly Gln Thr Ser Pro Gly Asn Cys
    1475                1480                1485

Val Leu Leu Asp Pro Lys Gly Thr Trp Lys His Glu Lys Cys Asn Ser
    1490                1495                1500

Val Lys Asp Gly Ala Ile Cys Tyr Lys Pro Thr Lys Ser Lys Lys Leu
1505                1510                1515                1520

Ser Arg Leu Thr Tyr Ser Ser Arg Cys Pro Ala Ala Lys Glu Asn Gly
        1525                1530                1535

Ser Arg Trp Ile Gln Tyr Lys Gly His Cys Tyr Lys Ser Asp Gln Ala
        1540                1545                1550

Leu His Ser Phe Ser Glu Ala Lys Lys Leu Cys Ser Lys His Asp His
    1555                1560                1565

Ser Ala Thr Ile Val Ser Ile Lys Asp Glu Asp Glu Asn Lys Phe Val
    1570                1575                1580

Ser Arg Leu Met Arg Glu Asn Asn Asn Ile Thr Met Arg Val Trp Leu
1585                1590                1595                1600

Gly Leu Ser Gln His Ser Val Asp Gln Ser Trp Ser Trp Leu Asp Gly
        1605                1610                1615

Ser Glu Val Thr Phe Val Lys Trp Glu Asn Lys Ser Lys Ser Gly Val
        1620                1625                1630

Gly Arg Cys Ser Met Leu Ile Ala Ser Asn Glu Thr Trp Lys Lys Val
    1635                1640                1645

Glu Cys Glu His Gly Phe Gly Arg Val Val Cys Lys Val Pro Leu Gly
    1650                1655                1660

Pro Asp Tyr Thr Ala Ile Ala Ile Ile Val Ala Thr Leu Ser Ile Leu
1665                1670                1675                1680

Val Leu Met Gly Gly Leu Ile Trp Phe Leu Phe Gln Arg His Arg Leu
        1685                1690                1695

His Leu Ala Gly Phe Ser Ser Val Arg Tyr Ala Gln Gly Val Asn Glu
        1700                1705                1710

Asp Glu Ile Met Leu Pro Ser Phe His Asp
    1715                1720

<210> SEQ ID NO 2
<211> LENGTH: 5169
<212> TYPE: DNA
<213> ORGANISM: Homo sapiens

<400> SEQUENCE: 2
atgaggacag gctgggcgca cccctcgccg cccggcgggg ctcctcatgc tgctcttctg      60
gttcttcgat ctcgcggagc cctctggccg cgcactaatg acccccttcac catcgtccat    120 ggaaatacgg gcaagtgcat caagccagtg tatggctgga tagtagcaga cgactgtgat    180
gaaactgagg acaagttatg gaagtgggtg tcccagcatc ggctctttca tttgcactcc    240

```
caaaagtgcc ttggcctcga tattaccaaa tcggtaaatg agctgagaat gttcagctgt      300
gactccagtg ccatgctgtg gtggaaatgt gagcaccact ctctgtacgg agctgcccgg      360
tactggctgg ctctgaagga tggacatggc acagcaatct caaatgcatc tgatgtctgg      420
aagaaaggag gctcagagga aagcctttgt gaccagcctt atcatgagat ctataccaga      480
gatgggaact cttatgggag accttgtgaa tttccattct taattgatgg acctggcat       540 catgattgca ttcttgatga agatcatagt gggccatggt gtgccaccac cttaaattat      600
gaatatgacc gaaagtgggg catctgctta aagcctgaaa acggttgtga agataattgg      660
gaaaagaacg agcagtttgg aagttgctac caatttaata ctcagacggc tctttcttgg      720
aaagaagctt atgtttcatg tcagaatcaa ggagctgatt tactgagcat caacagtgct      780
gctgaattaa cttaccttaa agaaaaagaa ggcattgcta agattttctg gattggttta      840
aatcagctat actctgctag aggctgggaa tggtcagacc acaaaccatt aaactttctc      900
aactgggatc cagacaggcc cagtgcacct actataggtg gctccagctg tgcaagaatg      960
gatgctgagt ctggtctgtg gcagagcttt tcctgtgaag ctcaactgcc ctatgtctgc     1020
aggaaaccat taaataatac agtggagtta acagatgtct ggacatactc agatacccgc     1080
tgtgatgcag gctggctgcc aaataatgga ttttgctatc tgctggtaaa tgaaagtaat     1140
tcctgggata aggcacatgc gaaatgcaaa gccttcagta gtgacctaat cagcattcat     1200
tctctagcag atgtggaggt ggttgtcaca aaactccata atgaggatat caaagaagaa     1260
gtgtggatag gccttaagaa cataaacata ccaactttat ttcagtggtc agatggtact     1320
gaagttactc taacatattg ggatgagaat gagccaaatg ttccctacaa taagacgccc     1380
aactgtgttt cctacttagg agagctaggt cagtggaaag tccaatcatg tgaggagaaa     1440
ctaaaatatg tatgcaagag aaagggagaa aaactgaatg acgcaagttc tgataagatg     1500
tgtcctccag atgagggctg gaagagacat ggagaaacct gttacaagat ttatgaggat     1560
gaggtccctt ttgaacaaaa ctgcaatctg actatcacta gcagatttga gcaagaatac     1620
ctaaatgatt tgatgaaaaa gtatgataaa tctctaagaa aatacttctg gactggcctg     1680
agagatgtag attcttgtgg agagtataac tgggcaactt ttggtggaag aaggcgggct     1740 gtaaccttt ccaactggaa ttttcttgag ccagcttccc cgggcggctg cgtggctatg     1800
tctactggaa agtctgttgg aaagtgggag gtgaaggact gcagaagctt caaagcactt     1860
tcaatttgca agaaaatgag tggaccccctt gggcctgaag aagcatcccc taagcctgat     1920 gaccccgtgtc ctgaaggctg gcagagtttc cccgcaagtc tttcttgtta taaggtattc     1980
catgcagaaa gaattgtaag aaagaggaac tgggaagaag ctgaacgatt ctgccaagcc     2040
cttggagcac acctttctag cttcagccat gtggatgaaa taaggaatt tcttcacttt     2100 ttaacggacc agttcagtgg ccagcattgg ctgtggattg gtttgaataa aaggagccca     2160
gatttacaag gatcctggca atggagtgat cgtacaccag tgtctactat tatcatgcca     2220
aatgagtttc agcaggatta tgacatcaga gactgtgctg ctgtcaaggt atttcatagg     2280
ccatggcgaa gaggctggca tttctatgat gatagagaat ttatttattt gaggcctttt     2340
gcttgtgata caaaacttga atgggtgtgc caaattccaa aaggccgtac tccaaaaaca     2400
ccagactggt acaatccaga ccgtgctgga attcatggac ctccactat aattgaagga     2460 agtgaatatt ggtttgttgc tgatcttcac ctaaactatg aagaagccgt cctgtactgt     2520
gccagcaatc acagctttct tgcgactata acatcttttg tgggactaaa agccatcaaa     2580
aacaaaatag caaatatatc tggtgatgga cagaagtggt ggataagaat tagcgagtgg     2640
```

```
ccaatagatg atcattttac atactcacga tatccatggc accgctttcc tgtgacattt    2700
ggagaggaat gcttgtacat gtctgccaag acttggctta tcgacttagg taaaccaaca    2760
gactgtagta ccaagttgcc cttcatctgt gaaaaatata atgtttcttc gttagagaaa    2820
tacagcccag attctgcagc taaagtgcaa tgttctgagc aatggattcc ttttcagaat    2880
aagtgttttc taaagatcaa acccgtgtct ctcacatttt ctcaagcaag cgatacctgt    2940
cactcctatg gtggcaccct tccttcagtg ttgagccaga ttgaacaaga ctttattaca    3000
tccttgcttc cggatatgga agctacttta tggattggtt tgcgctggac tgcctatgaa    3060
aagataaaca aatggacaga taacagagag ctgacgtaca gtaactttca cccattattg    3120
gttagtggga ggctgagaat accagaaaat ttttttgagg aagagtctcg ctaccactgt    3180
gccctaatac tcaacctcca aaaatcaccg tttactggga cgtggaattt tacatcctgc    3240
agtgaacgcc actttgtgtc tctctgtcag aaatattcag aagttaaaag cagacagacg    3300
ttgcagaatg cttcagaaac tgtaaagtat ctaaataatc tgtacaaaat aatcccaaag    3360
actctgactt ggcacagtgc taaaagggag tgtctgaaaa gtaacatgca gctggtgagc    3420
atcacggacc cttaccagca ggcattcctc agtgtgcagg cgctccttca caactcttcc    3480
ttatggatcg gactcttcag tcaagatgat gaactcaact ttggttggtc agatgggaaa    3540
cgtcttcatt ttagtcgctg ggctgaaact aatgggcaac tcgaagactg tgtagtatta    3600
gacactgatg gattctggaa aacagttgat tgcaatgaca atcaaccagg tgctatttgc    3660
tactattcag gaaatgagac tgaaaaagag gtcaaaccag ttgacagtgt taaatgtcca    3720
tctcctgttc taaatactcc gtggatacca tttcagaact gttgctacaa tttcataata    3780
acaaagaata ggcatatggc aacaacacag gatgaagttc atactaaatg ccagaaactg    3840
aatccaaaat cacatattct gagtattcga gatgaaaagg agaataactt tgttcttgag    3900
caactgctgt acttcaatta tatggcttca tgggtcatgt taggaataac ttatagaaat    3960
aattctctta tgtggtttga taagacccca ctgtcatata cacattggag agcaggaaga    4020
ccaactataa aaaatgagaa gttttttggct ggttttaagta ctgacggctt ctgggatatt    4080 caaacccttta aagttattga agaagcagtt tattttcacc agcacagcat tcttgcttgt    4140
aaaattgaaa tggttgacta caaagaagaa cataatacta cactgccaca gtttatgcca    4200
tatgaagatg gtatttacag tgttattcaa aaaaaggtaa catggtatga agcattaaac    4260
atgtgttctc aaagtggagg tcacttggca agcgttcaca accaaaatgg ccagctcttt    4320
ctggaagata tttgtaaaacg tgatggattt ccactatggg ttgggctctc aagtcatgat    4380
ggaagtgaat caagttttga atggtctgat ggtagtacat ttgactatat cccatggaaa    4440
ggccaaacat ctcctggaaa ttgtgttctc ttggatccaa aaggaacttg gaaacatgaa    4500
aaatgcaact ctgttaagga tggtgctatt tgttataaac ctacaaaatc taaaaagctg    4560
tcccgtctta catattcatc aagatgtcca gcagcaaaag agaatgggtc acggtggatc    4620
cagtacaagg gtcactgtta caagtctgat caggcattgc acagtttttc agaggccaaa    4680
aaattgtgtt caaacatga tcactctgca actatcgttt ccataaaaga tgaagatgag    4740
aataaatttg tgagcagact gatgagggaa aataataaca ttaccatgag agtttggctt    4800
ggattatctc aacattctgt tgaccagtct tggagttggt tagatggatc agaagtgaca    4860
tttgtcaaat gggaaaataa agtaagagt ggtgttggaa gatgtagcat gttgatagct    4920
tcaaatgaaa cttggaaaaa agttgaatgt gaacatggtt ttggaagagt tgtctgcaaa    4980
gtgcctctgg gccctgatta cacagcaata gctatcatag ttgccacact aagtatctta    5040
```

```
gttctcatgg gcggactgat ttggttcctc ttccaaaggc accgtttgca cctggcgggt    5100
ttctcatcag ttcgatatgc acaaggagtg aatgaagatg agattatgct tccttctttc    5160
catgactaa                                                            5169
```

<210> SEQ ID NO 3
<211> LENGTH: 116
<212> TYPE: PRT
<213> ORGANISM: Homo sapiens

<400> SEQUENCE: 3

```
Thr Val Asp Cys Asn Asp Asn Gln Pro Gly Ala Ile Cys Tyr Tyr Ser
 1               5                  10                  15

Gly Asn Glu Thr Glu Lys Glu Val Lys Pro Val Asp Ser Val Lys Cys
            20                  25                  30

Pro Ser Pro Val Leu Asn Thr Pro Trp Ile Pro Phe Gln Asn Cys Cys
        35                  40                  45

Tyr Asn Phe Ile Ile Thr Lys Asn Arg His Met Ala Thr Thr Gln Asp
    50                  55                  60

Glu Val His Thr Lys Cys Gln Lys Leu Asn Pro Lys Ser His Ile Leu
65                  70                  75                  80

Ser Ile Arg Asp Glu Lys Glu Asn Asn Phe Val Leu Glu Gln Leu Leu
                85                  90                  95

Tyr Phe Asn Tyr Met Ala Ser Trp Val Met Leu Gly Ile Thr Tyr Arg
            100                 105                 110

Asn Asn Ser Leu
        115
```

<210> SEQ ID NO 4
<211> LENGTH: 36
<212> TYPE: PRT
<213> ORGANISM: Homo sapiens

<400> SEQUENCE: 4

```
Ser Gln His Arg Leu Phe His Leu His Ser Gln Lys Cys Leu Gly Leu
 1               5                  10                  15

Asp Ile Thr Lys Ser Val Asn Glu Leu Arg Met Phe Ser Cys Asp Ser
            20                  25                  30

Ser Ala Met Leu
        35
```

<210> SEQ ID NO 5
<211> LENGTH: 349
<212> TYPE: DNA
<213> ORGANISM: Homo sapiens

<400> SEQUENCE: 5

```
aacagttgat tgcaatgaca atcaaccagg tgctatttgc tactattcag gaaatgagac      60 tgaaaagag gtcaaaccag ttgacagtgt aaatgtcca tctcctgttc taaatactcc      120
gtggatacca tttcagaact gttgctacaa tttcataata acaaagaata ggcatatggc     180
aacaacacag gatgaagttc atactaaatg ccagaaactg aatccaaaat cacatattct     240
gagtattcga gatgaaaagg agaataactt tgttcttgag caactgctgt acttcaatta     300
tatggcttca tgggtcatgt taggaataac ttatagaaat aaktctctt                 349
```

<210> SEQ ID NO 6
<211> LENGTH: 152
<212> TYPE: DNA
<213> ORGANISM: Homo sapiens

```
<400> SEQUENCE: 6
attaatatgc tgtggaagtg ggtgtcccag catcggctct ttcatttgca ctcccaaaag      60
tgccttggcc tcgatattac caaatcggta aatgagctga gaatgttcag ctgtgactcc    120
agtgccatgc tgtggtggaa atgcgagcac ca                                   152

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (6)
<223> OTHER INFORMATION: a, c, g, t, unknown or other
<220> FEATURE:
<221> NAME/KEY: modified_base
<222> LOCATION: (12)
<223> OTHER INFORMATION: a, c, g, t, unknown or other

<400> SEQUENCE: 7
gayacngayg gnttytggaa                                                  20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (18)
<223> OTHER INFORMATION: a, c, g, t, unknown or other

<400> SEQUENCE: 8
tacaccaarc trttytgncg                                                  20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (9)
<223> OTHER INFORMATION: a, c, g, t, unknown or other

<400> SEQUENCE: 9
aayatgctnt ggaartgggt                                                  20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tgrtgytcrc ayttccacca                                                  20

<210> SEQ ID NO 11
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (6)
<223> OTHER INFORMATION: a, c, g, t, unknown or other
<220> FEATURE:
<221> NAME/KEY: modified_base
<222> LOCATION: (12)
<223> OTHER INFORMATION: a, c, g, t, unknown or other

<400> SEQUENCE: 11
gayacngayg gnttytggaa                                              20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (3)
<223> OTHER INFORMATION: a, c, g, t, unknown or other

<400> SEQUENCE: 12
gcngtyttrt craaccacat                                              20

<210> SEQ ID NO 13
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gctctagaaa catgacccat gaagcc                                       26

<210> SEQ ID NO 14
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gctctagaca tcggctcttt catttgt                                      27

<210> SEQ ID NO 15
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
cgggattcac agttgattgc aatgaca                                      27

<210> SEQ ID NO 16
<211> LENGTH: 35
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 16
gactagtctg cagaattctt tttttttttt ttttt                                35

<210> SEQ ID NO 17
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gactagtctg cagaattc                                                   18

<210> SEQ ID NO 18
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
cgggatccct ctggccgcgc actaatga                                        28

<210> SEQ ID NO 19
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ccgctcgagc tgtggatacc agcacatgcc t                                    31

<210> SEQ ID NO 20
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
gatgggaact cttatgggag acct                                            24

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
tgatgcaggc tggctgccaa ataa                                            24

<210> SEQ ID NO 22
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 22
aactgggcaa ctgttggtgg aaga                                            24

<210> SEQ ID NO 23
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
atggcgaaga ggctggcatt tcta                                            24

<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
ctcaagcaag cgatacctgt cact                                            24

<210> SEQ ID NO 25
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
tgggcaactc gaagactgtg tagt                                            24

<210> SEQ ID NO 26
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
caccagcaca gcattcttgc ttgt                                            24

<210> SEQ ID NO 27
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
atttgtgagc agactgatga ggga                                            24

<210> SEQ ID NO 28
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
```
cggaattcga tctcatgata aggctggtca ca                                    32

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
gtggatccag tacaagggtc a                                                21

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
accaaatcag tccgcccatg a                                                21

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
atggggaagg tgaaggtcgg a                                                21

<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
aggggccatc cacagtcttc t                                                21

<210> SEQ ID NO 33
<211> LENGTH: 11
<212> TYPE: PRT
<213> ORGANISM: Homo sapiens

<400> SEQUENCE: 33

Ala Thr Thr Gln Asp Glu Val His Thr Lys Cys
 1               5                  10

<210> SEQ ID NO 34
<211> LENGTH: 13
<212> TYPE: PRT
<213> ORGANISM: Homo sapiens

<400> SEQUENCE: 34

Thr Glu Lys Glu Val Lys Pro Val Asp Ser Val Lys Cys
 1               5                  10

<210> SEQ ID NO 35
<211> LENGTH: 15

```
<212> TYPE: PRT
<213> ORGANISM: Homo sapiens

<400> SEQUENCE: 35

Lys Cys Leu Gly Leu Asp Ile Thr Lys Ser Val Asn Glu Leu Arg
  1               5                  10                  15

<210> SEQ ID NO 36
<211> LENGTH: 1723
<212> TYPE: PRT
<213> ORGANISM: Mus musculus

<400> SEQUENCE: 36

Met Arg Thr Gly Arg Val Thr Pro Gly Leu Ala Ala Gly Leu Leu
  1               5                  10                  15

Leu Leu Leu Arg Ser Phe Gly Leu Val Glu Pro Ser Glu Ser Gly
                 20                  25                  30

Asn Asp Pro Phe Thr Ile Val His Glu Asn Thr Gly Lys Cys Ile Gln
                 35                  40                  45

Pro Leu Ser Asp Trp Val Val Ala Gln Asp Cys Ser Gly Thr Asn Asn
                 50                  55                  60

Met Leu Trp Lys Trp Val Ser Gln His Arg Leu Phe His Leu Glu Ser
 65                  70                  75                  80

Gln Lys Cys Leu Gly Leu Asp Ile Thr Lys Ala Thr Asp Asn Leu Arg
                 85                  90                  95

Met Phe Ser Cys Asp Ser Thr Val Met Leu Trp Trp Lys Cys Glu His
                100                 105                 110

His Ser Leu Tyr Thr Ala Ala Gln Tyr Arg Leu Ala Leu Lys Asp Gly
                115                 120                 125

Tyr Ala Val Ala Asn Thr Asn Thr Ser Asp Val Trp Lys Lys Gly Gly
                130                 135                 140

Ser Glu Glu Asn Leu Cys Ala Gln Pro Tyr His Glu Ile Tyr Thr Arg
145                 150                 155                 160

Asp Gly Asn Ser Tyr Gly Arg Pro Cys Glu Phe Pro Phe Leu Ile Gly
                165                 170                 175

Glu Thr Trp Tyr His Asp Cys Ile His Asp Glu Asp His Ser Gly Pro
                180                 185                 190

Trp Cys Ala Thr Thr Leu Ser Tyr Glu Tyr Asp Gln Lys Trp Gly Ile
                195                 200                 205

Cys Leu Leu Pro Glu Ser Gly Cys Glu Gly Asn Trp Glu Lys Asn Glu
                210                 215                 220

Gln Ile Gly Ser Cys Tyr Gln Phe Asn Asn Gln Glu Ile Leu Ser Trp
225                 230                 235                 240

Lys Glu Ala Tyr Val Ser Cys Gln Asn Gln Gly Ala Asp Leu Leu Ser
                245                 250                 255

Ile His Ser Ala Ala Glu Leu Ala Tyr Ile Thr Gly Lys Glu Asp Ile
                260                 265                 270

Ala Arg Leu Val Trp Leu Gly Leu Asn Gln Leu Tyr Ser Ala Arg Gly
                275                 280                 285

Trp Glu Trp Ser Asp Phe Arg Pro Leu Lys Phe Leu Asn Trp Asp Pro
                290                 295                 300

Gly Thr Pro Val Ala Pro Val Ile Gly Gly Ser Ser Cys Ala Arg Met
305                 310                 315                 320

Asp Thr Glu Ser Gly Leu Trp Gln Ser Val Ser Cys Glu Ser Gln Gln
                325                 330                 335
```

-continued

Pro Tyr Val Cys Lys Lys Pro Leu Asn Asn Thr Leu Glu Leu Pro Asp
            340                 345                 350

Val Trp Thr Tyr Thr Asp Thr His Cys His Val Gly Trp Leu Pro Asn
            355                 360                 365

Asn Gly Phe Cys Tyr Leu Leu Ala Asn Glu Ser Ser Ser Trp Asp Ala
            370                 375                 380

Ala His Leu Lys Cys Lys Ala Phe Gly Ala Asp Leu Ile Ser Met His
385                 390                 395                 400

Ser Leu Ala Asp Val Glu Val Val Thr Lys Leu His Asn Gly Asp
            405                 410                 415

Val Lys Lys Glu Ile Trp Thr Gly Leu Lys Asn Thr Asn Ser Pro Ala
            420                 425                 430

Leu Phe Gln Trp Ser Asp Gly Thr Glu Val Thr Leu Thr Tyr Trp Asn
            435                 440                 445

Glu Asn Glu Pro Ser Val Pro Phe Asn Lys Thr Pro Asn Cys Val Ser
            450                 455                 460

Tyr Leu Gly Lys Leu Gly Gln Trp Lys Val Gln Ser Cys Glu Lys Lys
465                 470                 475                 480

Leu Arg Tyr Val Cys Lys Lys Gly Glu Ile Thr Lys Asp Ala Glu
            485                 490                 495

Ser Asp Lys Leu Cys Pro Pro Asp Glu Gly Trp Lys Arg His Gly Glu
            500                 505                 510

Thr Cys Tyr Lys Ile Tyr Glu Lys Glu Ala Pro Phe Gly Thr Asn Cys
            515                 520                 525

Asn Leu Thr Ile Thr Ser Arg Phe Glu Gln Phe Leu Asn Tyr Met
            530                 535                 540

Met Lys Asn Tyr Asp Lys Ser Leu Arg Lys Tyr Phe Trp Thr Gly Leu
545                 550                 555                 560

Arg Asp Pro Asp Ser Arg Gly Glu Tyr Ser Trp Ala Val Ala Gln Gly
            565                 570                 575

Val Lys Gln Ala Val Thr Phe Ser Asn Trp Asn Phe Leu Glu Pro Ala
            580                 585                 590

Ser Pro Gly Gly Cys Val Ala Met Ser Thr Gly Lys Thr Leu Gly Lys
            595                 600                 605

Trp Glu Val Lys Asn Cys Arg Ser Phe Arg Ala Leu Ser Ile Cys Lys
610                 615                 620

Lys Val Ser Glu Pro Gln Glu Pro Glu Glu Ala Ala Pro Lys Pro Asp
625                 630                 635                 640

Asp Pro Cys Pro Glu Gly Trp His Thr Phe Pro Ser Ser Leu Ser Cys
            645                 650                 655

Tyr Lys Val Phe His Ile Glu Arg Ile Val Arg Lys Asn Trp Glu
            660                 665                 670

Glu Ala Glu Arg Phe Cys Gln Ala Leu Gly Ala His Leu Pro Ser Phe
            675                 680                 685

Ser Arg Arg Glu Glu Ile Lys Asp Phe Val His Leu Leu Lys Asp Gln
            690                 695                 700

Phe Ser Gly Gln Arg Trp Leu Trp Ile Gly Leu Asn Lys Arg Ser Pro
705                 710                 715                 720

Asp Leu Gln Gly Ser Trp Gln Trp Ser Asp Arg Thr Pro Val Ser Ala
            725                 730                 735

Val Met Met Glu Pro Glu Phe Gln Gln Asp Phe Asp Ile Arg Asp Cys
            740                 745                 750

Ala Ala Ile Lys Val Leu Asp Val Pro Trp Arg Arg Val Trp His Leu
            755                 760                 765

-continued

```
Tyr Glu Asp Lys Asp Tyr Ala Tyr Trp Lys Pro Phe Ala Cys Asp Ala
    770                 775                 780

Lys Leu Glu Trp Val Cys Gln Ile Pro Lys Gly Ser Thr Pro Gln Met
785                 790                 795                 800

Pro Asp Trp Tyr Asn Pro Glu Arg Thr Gly Ile His Gly Pro Pro Val
                805                 810                 815

Ile Ile Glu Gly Ser Glu Tyr Trp Phe Val Ala Asp Pro His Leu Asn
            820                 825                 830

Tyr Glu Glu Ala Val Leu Tyr Cys Ala Ser Asn His Ser Phe Leu Ala
        835                 840                 845

Thr Ile Thr Ser Phe Thr Gly Leu Lys Ala Ile Lys Asn Lys Leu Ala
    850                 855                 860

Asn Ile Ser Gly Glu Gln Lys Trp Val Lys Thr Ser Glu Asn
865                 870                 875                 880

Pro Ile Asp Arg Tyr Phe Leu Gly Ser Arg Arg Leu Trp His His
                885                 890                 895

Phe Pro Met Thr Phe Gly Asp Glu Cys Leu His Met Ser Ala Lys Thr
            900                 905                 910

Trp Leu Val Asp Leu Ser Lys Arg Ala Asp Cys Asn Ala Lys Leu Pro
        915                 920                 925

Phe Ile Cys Glu Arg Tyr Asn Val Ser Ser Leu Glu Lys Tyr Ser Pro
    930                 935                 940

Asp Pro Ala Ala Lys Val Gln Cys Thr Glu Lys Trp Ile Pro Phe Gln
945                 950                 955                 960

Asn Lys Cys Phe Leu Lys Val Asn Ser Gly Pro Val Thr Phe Ser Gln
                965                 970                 975

Ala Ser Gly Ile Cys His Ser Tyr Gly Gly Thr Leu Pro Ser Val Leu
            980                 985                 990

Ser Arg Gly Glu Gln Asp Phe Ile Ile Ser Leu Leu Pro Glu Met Glu
        995                 1000                1005

Ala Ser Leu Trp Ile Gly Leu Arg Trp Thr Ala Tyr Glu Arg Ile Asn
    1010                1015                1020

Arg Trp Thr Asp Asn Arg Glu Leu Thr Tyr Ser Asn Phe His Pro Leu
1025                1030                1035                1040

Leu Val Gly Arg Arg Leu Ser Ile Pro Thr Asn Phe Phe Asp Asp Glu
                1045                1050                1055

Ser His Phe His Cys Ala Leu Ile Leu Asn Leu Lys Lys Ser Pro Leu
            1060                1065                1070

Thr Gly Thr Trp Asn Phe Thr Ser Cys Ser Glu Arg His Ser Leu Ser
        1075                1080                1085

Leu Cys Gln Lys Tyr Ser Glu Thr Glu Asp Gly Gln Pro Trp Glu Asn
    1090                1095                1100

Thr Ser Lys Thr Val Lys Tyr Leu Asn Asn Leu Tyr Lys Ile Ile Ser
1105                1110                1115                1120

Lys Pro Leu Thr Trp His Gly Ala Leu Lys Glu Cys Met Lys Glu Lys
                1125                1130                1135

Met Arg Leu Val Ser Ile Thr Asp Pro Tyr Gln Gln Ala Phe Leu Ala
            1140                1145                1150

Val Gln Ala Thr Leu Arg Asn Ser Ser Phe Trp Ile Gly Leu Ser Ser
        1155                1160                1165

Gln Asp Asp Glu Leu Asn Phe Gly Trp Ser Asp Gly Lys Arg Leu Gln
    1170                1175                1180
```

-continued

Phe Ser Asn Trp Ala Gly Ser Asn Glu Gln Leu Asp Asp Cys Val Ile
1185                1190                1195                1200

Leu Asp Thr Asp Gly Phe Trp Lys Thr Ala Asp Cys Asp Asn Gln
        1205                1210                1215

Pro Gly Ala Ile Cys Tyr Tyr Pro Gly Asn Glu Thr Glu Glu Val
        1220                1225                1230

Arg Ala Leu Asp Thr Ala Lys Cys Pro Ser Pro Val Gln Ser Thr Pro
        1235                1240                1245

Trp Ile Pro Phe Gln Asn Ser Cys Tyr Asn Phe Met Ile Thr Asn Asn
    1250                1255                1260

Arg His Lys Thr Val Thr Pro Glu Glu Val Gln Ser Thr Cys Glu Lys
1265                1270                1275                1280

Leu His Pro Lys Ala His Ser Leu Ser Ile Arg Asn Glu Glu Glu Asn
        1285                1290                1295

Thr Phe Val Val Glu Gln Leu Leu Tyr Phe Asn Tyr Ile Ala Ser Trp
        1300                1305                1310

Val Met Leu Gly Ile Thr Tyr Glu Asn Asn Ser Leu Met Trp Phe Asp
        1315                1320                1325

Lys Thr Ala Leu Ser Tyr Thr His Trp Arg Thr Gly Arg Pro Thr Val
    1330                1335                1340

Lys Asn Gly Lys Phe Leu Ala Gly Leu Ser Thr Asp Gly Phe Trp Asp
1345                1350                1355                1360

Ile Gln Ser Phe Asn Val Ile Glu Glu Thr Leu His Phe Tyr Gln His
        1365                1370                1375

Ser Ile Ser Ala Cys Lys Ile Glu Met Val Asp Tyr Glu Asp Lys His
        1380                1385                1390

Asn Gly Thr Leu Pro Gln Phe Ile Pro Tyr Lys Asp Gly Val Tyr Ser
        1395                1400                1405

Val Ile Gln Lys Lys Val Thr Trp Tyr Glu Ala Leu Asn Ala Cys Ser
    1410                1415                1420

Gln Ser Gly Gly Glu Leu Ala Ser Val His Asn Pro Asn Gly Lys Leu
1425                1430                1435                1440

Phe Leu Glu Asp Ile Val Asn Arg Asp Gly Phe Pro Leu Trp Val Gly
        1445                1450                1455

Leu Ser Ser His Asp Gly Ser Glu Ser Ser Phe Glu Trp Ser Asp Gly
        1460                1465                1470

Arg Ala Phe Asp Tyr Val Pro Trp Gln Ser Leu Gln Ser Pro Gly Asp
        1475                1480                1485

Cys Val Val Leu Tyr Pro Lys Gly Ile Trp Arg Arg Glu Lys Cys Leu
        1490                1495                1500

Ser Val Lys Asp Gly Ala Ile Cys Tyr Lys Pro Thr Lys Asp Lys Lys
1505                1510                1515                1520

Leu Ile Phe His Val Lys Ser Ser Lys Cys Pro Val Ala Lys Arg Asp
        1525                1530                1535

Gly Pro Gln Trp Val Gln Tyr Gly Gly His Cys Tyr Ala Ser Asp Gln
        1540                1545                1550

Val Leu His Ser Phe Ser Glu Ala Lys Gln Val Cys Gln Glu Leu Asp
        1555                1560                1565

His Ser Ala Thr Val Val Thr Ile Ala Asp Glu Asn Glu Asn Lys Phe
    1570                1575                1580

Val Ser Arg Leu Met Arg Glu Asn Tyr Asn Ile Thr Met Arg Val Trp
1585                1590                1595                1600

Leu Gly Leu Ser Gln His Ser Leu Asp Gln Ser Trp Ser Trp Leu Asp
        1605                1610                1615

-continued

```
Gly Leu Asp Val Thr Phe Val Lys Trp Glu Asn Lys Thr Lys Asp Gly
            1620                1625                1630

Asp Gly Lys Cys Ser Ile Leu Ile Ala Ser Asn Glu Thr Trp Arg Lys
        1635                1640                1645

Val His Cys Ser Arg Gly Tyr Ala Arg Ala Val Cys Lys Ile Pro Leu
    1650                1655                1660

Ser Pro Asp Tyr Thr Gly Ile Ala Ile Leu Phe Ala Val Leu Cys Leu
1665            1670                1675                1680

Leu Gly Leu Ile Ser Leu Ala Ile Trp Phe Leu Leu Gln Arg Ser His
            1685                1690                1695

Ile Arg Trp Thr Gly Phe Ser Ser Val Arg Tyr Glu His Gly Thr Asn
                1700                1705                1710

Glu Asp Glu Val Met Leu Pro Ser Phe His Asp
            1715                1720
```

MONOCLONAL ANTIBODIES AGAINST DENDRITIC CELL RECEPTOR

CROSS-REFERENCE TO RELATED APPLICATIONS

This application is a continuation of application Ser. No. 11/068,882 filed Mar. 2, 2005, abandoned, which is a divisional of application Ser. No. 10/141,956, filed May 10, 2002, abandoned, which is a divisional of application Ser. No. 09/194,612, filed Mar. 18, 1999, U.S. Pat. No. 6,432,666, which is a 371 of PCT/NZ97/00068, filed May 19, 1997, which claims priority to New Zealand Application No. 286692 filed May 19, 1996, the entire contents of each of which are hereby incorporated by reference.

FIELD OF THE INVENTION

This invention relates to dendritic cell receptors. In particular, it relates to human DEC-205, to the production and use thereof, and to ligands which bind to it. Human DEC-205 and its ligands are useful in prophylaxis and therapy.

BACKGROUND OF THE INVENTION

Dendritic cells perform important immunoregulatory functions by presenting antigens in the form of peptides bound to cell-surface major histocompatibility complex (MHC) molecules to T cells. Identification of the mechanism by which this antigen presentation function is achieved therefore has important implications in manipulating immune response in prophylaxis and therapy, particularly in humans.

Jiang et al, *Nature* 375: 151-155 (1995) disclose a murine dendritic cell receptor having a molecular weight of 205 kDa (murine DEC-205). However, they do not disclose a receptor on human dendritic cells.

The applicant has now identified a receptor on human dendritic cells. It is broadly to this receptor (likely to be the human homolog of murine DEC-205) that the present invention is directed.

SUMMARY OF THE INVENTION

The present invention has a number of aspects. In a first aspect, the invention provides isolated human DEC-205 which has an approximate molecular weight of 198-205 kDa and which includes the following amino acid sequences:

(i)
(SEQ ID NO: 3)
TVDCNDNQPGAICYYSGNETEKEVKPVDSVKCPSPVLNTPWIPF

QNCCYNFIITKNRHMATTQDEVHTKCEKLHPKSHILSIRDEKE

NNFVLEQLLYFNYMASWVMLGITYRNNSL;
and (ii)
(SEQ ID NO: 4)
SQHRLFHLHSQKCLGLDITKSVNELRMFSCDSSAML;

or a functionally equivalent fragment thereof.

In a further aspect, the invention provides isolated human DEC-205 which comprises the amino acid sequence shown in FIG. 11 or a functionally equivalent fragment thereof.

In a still further aspect, the invention provides isolated mature human DEC-205, which comprises the amino acids 27 to 1722 shown for human DEC-205 in FIG. 11.

In yet a further aspect, the invention provides an extracellular domain of human DEC-205 or a functionally-equivalent fragment thereof.

In a preferred embodiment, the extracellular domain fragment includes at least a portion of carbohydrate recognition domain (CRD7), spacer, and a portion of carbohydrate recognition domain (CRD8) of human DEC-205 (amino acids 1208 to 1323 of the amino acid sequence of FIG. 11).

In a still further aspect, the invention provides a polynucleotide encoding human DEC-205 or its extracellular domain as defined above. This polynucleotide is preferably DNA, more preferably cDNA, but can also be RNA.

In a specific embodiment, the polynucleotide coding for human DEC-205 includes the following nucleotide sequences:

In a specific embodiment, the polynucleotide coding for human DEC-205 includes the following nucleotide sequences:

(iii)
(SEQ ID NO: 5)
A ACA GTT GAT TGC AAT GAC AAT CAA CCA GGTGCT ATT

TGC TAC TAT TCA GGA AAT GAG ACT GAA AAA GAG GTC

AAA CCA GTT GAC AGT GTT AAA TGT CCA TCT CCT GTT

CTA AAT ACT CCG TGG ATA CCA TTT CAG AAC TGT TGC

TAC AAT TTC ATA ATA ACA AAG AAT AGG CAT ATG GCA

ACA ACA CAG GAT GAA GTT CAT ACT AAA TGC CAG AAA

CTG AAT CCA AAA TCA CAT ATT CTG AGT ATT CGA GAT

GAA AAG GAG AAT AAC TTT GTT CTT GAG CAA CTG CTG

TAC TTC AAT TAT ATGGCT TCA TGG GTC ATG TTA GGA

ATA ACT TAT AGA AAT AAX TCT CTT;
and (iv)
(SEQ ID NO: 6)
ATT AAT ATG CTG TGG AAG TGG GTG TCC CAG CAT CGG

CTC TTT CAT TTG CAC TCC CAA AAG TGC CTT GGC CTC

GAT ATT ACC AAA TCG GTA AAT GAG CTG AGA ATG TTCAGC

TGT GAC TCC AGTGCC ATG CTG TGG TGG AAA TGC GAG CAC

CA wherein X is T or G.

In a further embodiment, the polynucleotide comprises part or all of the nucleotide sequence of FIG. 10.

In yet a further aspect, the invention provides a vector including a polynucleotide as defined above.

In still a further aspect, the invention provides a method of producing human DEC-205, the extracellular domain thereof or a functional fragment comprising the steps of:

(a) culturing a host cell which has been transformed or transfected with a vector as defined above to express the encoded human DEC-205, extracellular domain or fragment; and (b) recovering the expressed human DEC-205, extracellular domain or fragment.

As yet an additional aspect, the invention provides a ligand that binds to human DEC-205 or its extracellular domain as defined above.

Preferably, the ligand is an antibody or antibody binding fragment or carbohydrate bearing protein.

The antibody or antibody binding fragment can be used in methods for extracting or isolating activated dendritic cells.

In still a further aspect, the invention provides a construct for use in therapy or prophylaxis. The construct will usually be a ligand-antigen construct or a DEC-205-antigen construct although ligand-toxin and DEC-205-toxin constructs are also contemplated. The ligand-antigen construct preferably consists of an antibody or antibody binding fragment which binds to human DEC-205 and a host-protective antigen. The DEC-205-antigen construct preferably consists of at least the extracellular domain of human DEC-205 and a host-protective antigen.

In yet further aspects, the invention contemplates methods of therapy or prophylaxis which employ human DEC-205, ligands or constructs containing them.

In yet a further aspect, the invention provides a molecule (hapten) which may be used to generate antibodies for identifying or purifying human dendritic cells, which includes a peptide based upon part or all of the sequence of FIG. 11.

DESCRIPTION OF THE DRAWINGS

While the invention is broadly as defined above, it will be appreciated by those persons skilled in this art that it is not limited thereto and that it includes embodiments more particularly described below. It will also be better understood by reference to the accompanying drawings, in which

FIGS. 3A-1, 3A-2, and 3B shows protein similarity between human and mouse DEC-205. A. The predicted amino acid sequence of human DEC-205 (SEQ ID NO: 1) is aligned with the mouse homolog (SEQ ID NO: 36). The regions corresponding to DEC-205 domain structure are bracketed. The positions of amino acids are shaded where there are identical or conservatively replaced amino acids between the sequences, and the asterisks indicate conserved cysteines. The diamonds indicates potential N-glycosylation sites conserved between the sequences. The arrow indicates one amino acid deletion in CRD-5 of human DEC-205. The circles indicate conserved potential serine-phosphorylation sites by protein kinase C (open circle) or casein kinase (closed circle). B. The % identity between human and mouse DEC-205 is indicated above each domain (boxed, See FIG. 2A for key);

FIG. 5 shows that human DEC-205 gene localizes on chromosome 2.
A somatic cell hybrid panel blot (restriction-digested with PstI) was subjected to Southern blot analysis with the [$^{32}$P] cysteine-rich domain probe. The final wash was 0.3×SSC at 65° C. The positions of the DNA molecular size standards are indicated to the right. The estimated molecular size of the probe-specific bands are indicated to the left. The asterisk indicates weakly hybridized bands. M, male; F, female;

FIGS. 10A, 10B, 10C, and 10D gives the DNA sequence for human DEC-205 (coding region only) (nucleotides 1-5166 of SEQ ID NO: 2);

FIGS. 11A and 11B gives the human DEC-205 amino acid sequence (SEQ ID NO: 1).

DETAILED DESCRIPTION OF THE INVENTION

A. Human DEC-205

Figure 1:
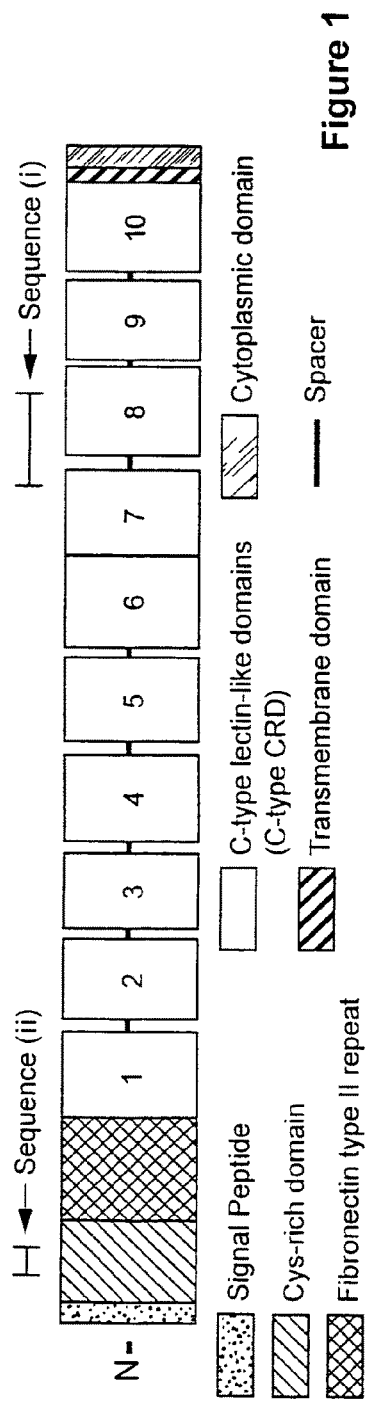
FIG. 1 shows the structure of human DEC-205.

The human DEC-205 of the invention is believed to be the human homolog of murine DEC-205 and has an approximate molecular weight of 198 to 205 kDa. It has the structure shown in FIGS. 1 and 2A. It also has the deduced amino acid sequence shown in FIG. 11.

Human DEC-205 can usefully be provided in a number of different forms. These include human DEC-205 itself, the "mature" form of human DEC-205, and the extracellular receptor domain of human DEC-205.

The "mature" form of human DEC-205 of the invention is human DEC-205 less its native amino-terminus leader or signal sequence, whereas the extracellular receptor domain is human DEC-205 lacking the signal sequence, the transmembrane region and cytoplasmic domain (where present).

The extracellular domain may be identified through commonly recognised criteria of extracellular amino acid sequences. The determination of appropriate criteria is known to those skilled in the art, and has been described, for example by Hopp et al., *Proc. Natl. Acad. Sci. USA* 78, 3824-3828 (1991); Kyte et al., *J. Mol. Biol.* 157, 105-132 (1982); Emini, *J. Virol* 55 836-839 (1985); Jameson et al. *CA BIOS* 4, 181-186 (1988); and Karplus et al. *Naturwissenschaften* 72 212-213 (1985). Amino acid domains predicted by these criteria to be surface exposed are characteristic of extracellular domains.

Figures 2, 3A:
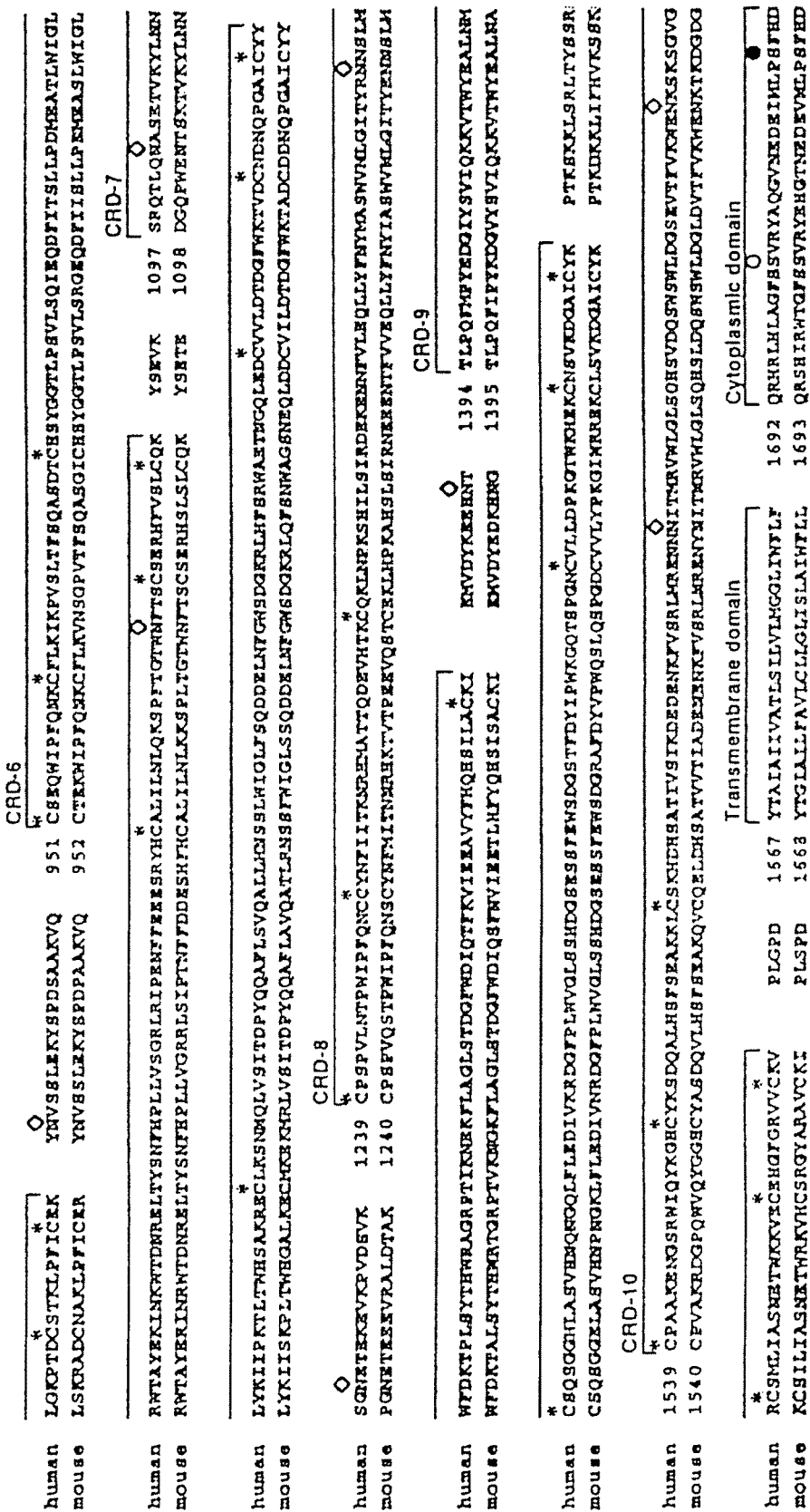

The amino acid sequences of the predicted regions for human DEC-205 are shown in FIG. 3A. These include the amino acid sequences for the signal peptide, cysteine-rich domain, fibronectin type II domain, Carbohydrate Recognition Domain-1, (CRD-1), CRD-2, CRD-3, CRD-4, CRD-5, CRD-6, CRD-7, CRD-8, CRD-9, CRD-10, transmembrane domain and cytoplasmic domain.

Human DEC-205 of the invention or its extracellular receptor domain (or parts thereof) may be prepared by methods known in the art. Such methods include protein synthesis from individual amino acids as described by Stuart and Young in "Solid Phase Peptide Synthesis", Second Edition, Pierce Chemical Company (1984). It is however preferred that human DEC-205 and/or its extracellular receptor domain or parts thereof be prepared by recombinant methods as will be detailed hereinafter.

Example 1 provides further details of human DEC-205.

Example 1

Langerhans cells were prepared from human skin. Epidermal cell suspensions were prepared from split thickness normal human breast skin by 30 min dispase (Boehringer-Mannheim, Mannheim, Germany; 0.5% in PBS) treatment at 37° C., followed by 10 min disaggregation in the presence of trypsin (0.25% in PBS), DNase I (5 U/ml in PBS) and 5 mM EDTA at room temperature. Langerhans cells were then enriched by Ficoll/Metrizoate gradient separation (d=1.077 g/cm³). Final cell suspensions contained 3-15% Langerhans cells as determined by HLA-DR positivity. Total RNA was extracted using Trizol reagent according to the manufacturer's instructions.

Degenerate primers were prepared on an Applied Biosystems DNA Synthesizer with the primer sequences (d) and (e) as set out below:

(d) 5'-GAX ACY GAX GGY TTX TGG AA-3' (SEQ ID NO: 7)

(e) 3'-GCY GTX TTZ TCZ AAC CAC AT-5' (SEQ ID NO: 8)

wherein X is C or T, Y is A, C, G or T, and Z is G or A.

Single stranded cDNA was prepared using total RNA and reverse transcribed by AMV reverse transcriptase using the 3' primer (e). Subsequently, the cDNA was amplified using the 5'(d) and 3'(e) primer using PCR amplification according to techniques known in the art.

The amplified products were run on a 2% agarose gel and visualized with ethidium bromide staining.

The DNA was purified and ligated into the T tailed pGEM vector (available from Promega) using standard techniques. The ligation mixture was transformed into competent *E. coli* JM 109 bacteria (available from Promega) which were grown on agar plates with appropriate antibiotic selection. Two colonies were isolated. DNA was prepared and digested with restriction enzymes.

Two inserts of the same size as the PCR product were sequenced by double-stranded DNA sequencing techniques using a Sequence Kit (Sequence 2.0 USB Lab Supply, Pierce). The two clones corresponded to human DEC-205.

The amino acid sequence of human DEC-205 was determined to include the following amino acid sequences:

(i)
(SEQ ID NO: 3)
TVDCNDNQPGAICYYSGNETEKEVKPVDSVKCPSPVLNTPWIPF

QNCCYNFIITKNRHMATTQDEVHTKCEKLHPKSHILSIRDEKE

NNFVLEQLLYFNYMASWVMLGITYRNNSL;
and (ii)
(SEQ ID NO: 4)
SQHRLFHLHSQKCLGLDITKSVNELRMFSCDSSAML.

Determination of these sequences was fundamental to isolating the cDNA for human DEC-205 detailed below.

In the partial sequences given above, individual amino acids are represented by the single letter code as follows:

| Amino Acid | Three-letter abbreviation | One-letter symbol |
|---|---|---|
| Alanine | Ala | A |
| Arginine | Arg | R |
| Asparagine | Asn | N |
| Aspartic acid | Asp | D |
| Asparagine or aspartic acid | Asx | B |
| Cysteine | Cys | C |
| Glutamine | Gln | Q |
| Glutamic Acid | Glu | E |
| Glutamine or glutamic acid | Glx | Z |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Unidentified | | X |

This code also applies to the predicted full sequence of FIG. 11, deduced from the cDNA encoding human DEC-205 isolated as described below.

B. Polynucleotides Encoding Human DEC-205

In another aspect of this invention, the applicants provide polynucleotides encoding human DEC-205 or its extracellular domain. These polynucleotides may be DNA (isolated from nature, synthesised or cDNA) or RNA. Most often, the polynucleotides will be DNA.

The polynucleotides of the invention specifically include those which include the nucleotides (iii)

(SEQ ID NO: 5)
```
A ACA GTT GAT TGC AAT GAC AAT CAA CCA GGTGCT ATT

TGC TAC TAT TCA GGA AAT GAG ACT GAA AAA GAG GTC

AAA CCA GTT GAC AGT GTT AAA TGT CCA TCT CCT GTT

CTA AAT ACT CCG TGG ATA CCA TTT CAG AAC TGT TGC

TAC AAT TTC ATA ATA ACA AAG AAT AGG CAT ATG GCA

ACA ACA CAG GAT GAA GTT CAT ACT AAA TGC CAG AAA

CTG AAT CCA AAA TCA CAT ATT CTG AGT ATT CGA GAT

GAA AAG GAG AAT AAC TTT GTT CTT GAG CAA CTG CTG

TAC TTC AAT TAT ATGGCT TCA TGG GTC ATG TTA GGA ATA

ACT TAT AGA AAT AAX TCT CTT;
```
and (iv)

(SEQ ID NO: 6)
```
ATT AAT ATG CTG TGG AAG TGG GTG TCC CAG CAT CGG

CTC TTT CAT TTG CAC TCC CAA AAG TGC CTT GGC CTC

GAT ATT ACC AAA TCG GTA AAT GAG CTG AGA ATG TTCAGC

TGT GAC TCC AGTGCC ATG CTG TGG TGG AAA TGC GAG CAC

CA
``` wherein X is T or G,
as well as the full nucleotide sequence shown in FIG. 10,
but are not limited thereto.

The invention also includes within its scope functional equivalents of these polynucleotides.

This aspect of the invention will now be illustrated by the following Examples.

Example 2

Experimental Procedures

Cell Culture—

The cell lines, HEL, K562, KG-1, THP-1, U937, Mann and Jurkat were obtained from the American Type Culture Collection (Rockville, Md.). L428 cells were provided by V. Diehl (Klinik for Innere Medizin, Cologne, Germany). HDLM2 and KMH2 cells were obtained from the German Collection of Micro-organisms and Cell Culture (Braunscfweig, Germany). Mono Mac 6 cells (Bufler et at (1995) *Eur. J. Immunol.* 25, 604-610) were provided by H. Engelmann (Institute for Immunology, Munchen, Germany). All cell lines were maintained in RPMI 1640, 10% fetal calf serum, 100 U/ml penicillin, 100 ug/ml streptomycin except that HDLM2 cells were with 20% fetal calf serum.

Isolation of Leukocytes—

Leukocyte populations were isolated using standard laboratory procedures.

Figure 2A:
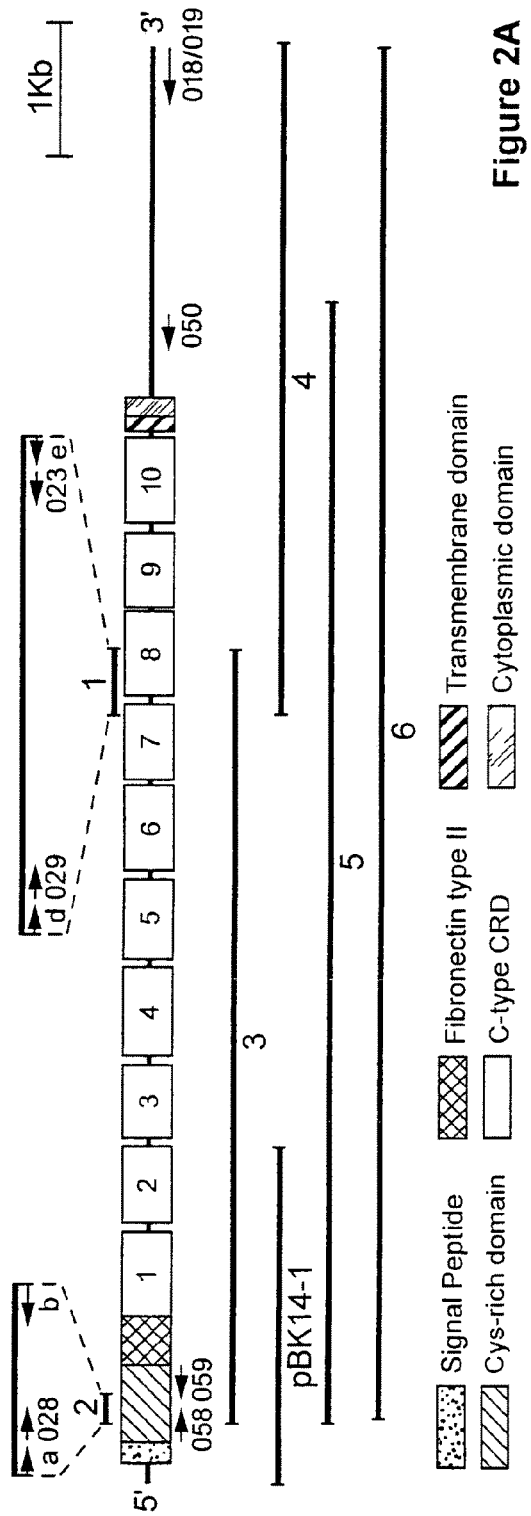
FIG. 2 shows the strategy for isolation of human DEC-205 cDNA.
A. A schematic presentation of human DEC-205 mRNA with the regions corresponding to DEC-205 domains. The positions of the primers used for the cDNA cloning and analysis are indicated with arrows. The positions of reverse transcriptase-polymerase chain reaction (RT-PCR) fragments 1 to 6 and the clone pBK14-1 are indicated with bars. B. RT-PCR amplification of fragment 1 and 2 from L428 and HEL cell line RNA. L428 and HEL cells were subjected to RT-PCR with two pairs of degenerate primers (DEC-a/-b, and DEC-d/-e), fractionated by electrophoresis through 2% agarose gel, and stained with ethidium bromide. C. RT-PCR and 3'-RACE amplification of fragment 3 and 4 from L428 cells using the primers 028/023 and 029/019, respectively. A cDNA pool of L428 cells was subjected to 3'-RACE and RT-PCR, electrophoresed through 0.8% agarose gel, and stained with ethidium bromide. The numbers on the top correspond to the name of fragment in FIG. 2A. The positions of DNA molecular size standard are indicated to the right. The estimated molecular size of the RT-PCR products are indicated to the left.

Isolation of cDNA encoding for human DEC-205—A set of degenerate oligonucleotide primers were designed based on the published amino acid sequence of mouse DEC-205 (Jiang et al (1995), above) and synthesized in house or by Life Technologies (Auckland, New Zealand) (see FIG. 2A). These primers were (SEQ ID NOS 9-12, respectively in order of appearance):

DEC-a (5'-AAYATGCTNTGGAARTGGGT-3'),
DEC-b (5'-TGRTGYTCRCAYTTCCACCA-3'),
DEC-d (5'-GAYACNGAYGGNTTYTGGAA-3') and
DEC-e (5'-GCNGTYTTRTCRAACCACAT-3'),
where Y=C or T, R=A or G, N=A or C or G or T. Total RNA isolated from L428 or HEL cells was reverse transcribed with avian myeloblastosis virus reverse transcriptase (Promega, Madison, Wis.) at 55° C. for 1 h using the primers DEC-b or DEC-e. PCR was performed using the resultant cDNA and Taq polymerase (Boehringer Mannheim, Auckland, New Zealand) with the primers DEC-a/-b for DEC-b-primed or DEC-d/-e for DEC-e-primed cDNAs. The PCR conditions used were the initial denaturation at 94° C. for 5 min, 35 cycles of denaturation at 94° C. for 1 min, annealing at 54° C. for 1 min, extension at 72° C. for 1 min, and the final extension at 72° C. for 5 min. The PCR reactions were fractionated with 2% agarose gel in 40 mM Tris-acetate, pH 8.3, 1 mM EDTA (TAE) buffer, and stained with 0.5 ug/ml ethidium bromide. The PCR fragments (fragment 1 and 2, see FIGS. 2A and 2B) were cloned into pGEM-T vector (Promega), and sequenced manually using Sequenase DNA sequencing kit (Amersham Life Science, Auckland, New Zealand).

A set of oligonucleotide primers nested within the DNA sequence of fragment 1 and 2 were synthesized (see FIG. 2A). These primers were:
023 (5'-GCTCTAGAAACATGACCCATGAAGCC-3' containing a XbaI site) (SEQ ID NO: 13),
028 (5'-GCTCTAGACATCGGCTCTTTCATTTGT-3' containing a XbaI site) (SEQ ID NO: 14) and
029 (5'-CGGGATTCACAGTTGATTGCAATGACA-3' containing a EcoRI site) (SEQ ID NO: 15)
where incorporated restriction sites are underlined. Two ug of poly(A) RNA from L428 cells was reverse transcribed with 200 U of SuperScriptII (LifeTechnolgies) at 45° C. for 1 h using an oligo d(T) adaptor primer 018 (5'-GACTAGTCTG-CAGAATTCTTTTTTTTTTTTTTTT-3' (SEQ ID NO: 16), containing a SpeI, PstI, and EcoRI sites). After heat-inactivation at 70° C. for 15 min, the reaction was incubated with 1 U RNaseH (Life Technologies) at 37° C. for 30 min, heat-inactivated at 70° C. for 15 min, and diluted to 1 ml with 10 mM Tris-HCl, pH 8.0, 1 mM EDTA (L428 cDNA pool). In order to isolate the fragment 3 (connecting the fragment 1 and 2) (see FIG. 2A), PCR was performed with 5 ul of L428 cDNA pool, the primers 028 and 023, and 2.5 U of Expand enzyme mix (BoehringerMannheim). The PCR conditions were the initial denaturation at 94° C. for 2 min, 10 cycles of 10 cycles of denaturation at 94° C. for 15 sec, annealing at 53° C. for 30 sec, and extension at 68° C. for 4 min, followed by 20 cycles of denaturation at 94° C. for 15 sec, annealing at 53° C. for 30 sec, and extension at 68° C. for 4 min plus additional 20 sec for each cycle, and the final extension at 68° C. for 15 min. 3'-rapid amplification of cDNA ends (3'-RACE) (Frohman et al (1988) Proc. Natl. Acad. Sci. USA 85, 8998-9002) was performed in order to isolate the fragment 4 (connecting the fragment 1 and the 3'-untranslated region of DEC-205) (see FIG. 2A). PCR was performed with 5 ul of L428 cDNA pool and the primer 029 and an adaptor primer 019 (5'-GACTAGTCTGCAGAATTC (SEQ ID NO: 17), containing a SpeI, PstI and EcoRI site), in the same conditions for the fragment 3. The PCR reactions were fractionated with 0.8% agarose gel in TAE buffer, and stained with ethidium bromide. Both the fragment 3 and 4 were restriction digested with XbaI and EcoRI, respectively, and cloned into pBluescript II (Stratagene, La Jolla, Calif.). The representative clones from the fragment 3 (pB38 f1) and 4 (pb30-3) were sequenced with a LI-COR automated sequencer (LI-COR, Lincoln, Nebr.) using SequiTherm cycle sequencing kit (Epicentre Technologies, Madison, Wis.). If required, these plasmids were subjected to exonucleaseIII-nested deletion using Erase-A-Base system (Promega), and used for sequencing.

An oligo dT-primed L428 cDNA library was prepared using ZAP Express cDNA Gigapack Cloning kit (Stratagene) according to manufacturer's instruction. The fragment 3 was labeled with [α-32P]dCTP (NEN) using Multiprime system (Amersham Life Science). The library was screened by plaque hybridization with the [$^{32}$P]fragment 3 using standard techniques (Sambrook, J., Fritsch, E. F., and Maniatis, T. (1989) *Molecular Cloning: A Laboratory Manual*, 2Ed., Cold Spring Harbour Laboratory, New York, USA). The specific activity of the probe was $0.8 \times 10^9$ cpm/ug DNA and used at $1 \times 10^6$ cpm/ml. The final wash was in 0.1×SSC, 0.5% SDS at 65° C. (1×SSC is 0.15 M NaCl, 15 mMM Na-citrate, pH7.0). Positive clones were converted to phagemid pBK-CMV (Stratagene) and sequenced using an automated sequencer.

In order to verify the DNA sequence obtained from the PCR clones, pB38f for fragment 3 and pB30-3 for fragment 4, the fragment 5 was PCR-amplified from L428 cDNA pool using primers 058(5'-CGGGATCCCTCTGGCCGCGCAC-TAATGA-3' (SEQ ID NO: 18) containing a BamHI site) and 050 (5'-CCGCTCGAGCTGTGGATACCAGCACATGCCT-3' (SEQ ID NO: 19) containing a XhoI site) (see FIG. 2A). The PCR conditions were identical to that for the fragment 3 except using longer extension period (6 min) for cycling. The fragment 5 was sequenced directly using the IRD40-labeled custom primers (MWG-Biotech, Ebersberg, Germany) and a LI-COR automated sequencer without cloning. These primers were (SEQ ID NOS 20-27 respectively in order of appearance):

```
IRD001
(5'-GATGGGAACTCTTATGGGAGACCT-3' at nucleotide 523-
555),

IRD002
(5'-TGATGCAGGCTGGCTGCCAAATAA-3' at nucleotide
1134-1157),

IRD003
(5'-AACTGGGCAACTGTTGGTGGAAGA-3' at nucleotide
1759-1782),

IRD004
(5'-ATGGCGAAGAGGCTGGCATTTCTA-3' at nucleotide
2334-2357),

IRD005
(5'-CTCAAGCAAGCGATACCTGTCACT-3' at nucleotide
2972-2995),

IRD006
(5'-TGGGCAACTCGAAGACTGTGTAGT-3' at nucleotide
3624-3647),

IRD007
(5'-CACCAGCACAGCATTCTTGCTTGT-3' at nucleotide
4168-4191)
and

IRD008
(5'-ATTTGTGAGCAGACTGATGAGGGA-3' at nucleotide
4797-4820).
```

The sequences of these primers were based on those of pb38f1 and pb30-3, and they were positioned as 540-650 bp apart, ensuring the generation of contigs overlapping by at least 100 bp after automated sequencing.

Southern Blot Analysis—

Genomic DNA was prepared from peripheral blood of patients with hematological disorders (each patient was karyotyped at Canterbury Health Laboratories, Christchurch, New Zealand). Approximately 8 ug of genomic DNA was digested with BglII, BamHI, EcoRI, or HindIII, fractionated in 0.8% agarose gel in 89 mM Tris-borate, pH 8.3, 2 mM EDTA, and transferred to Hybond N+ by capillary reaction. A PCR-fragment corresponding to the cyteine-rich domain was PCR-amplified from pBK14-1 using the primers 058 and 059 (5' CGGAATTCGATCTCATGATAAGGCTGGTCACA-3' (SEQ ID NO: 28) containing a EcoRI site) (see FIG. 2A). Briefly, PCR was performed with 2 ng of pBK14-1, the primer 058 and 059, and Taq polymerase. The PCR conditions used were the initial denaturation at 94° C. for 2 min, 30 cycles of denaturation at 94° C. for 15 sec, annealing at 55° C. for 15 sec, extension at 72° C. for 30 sec, and the final extension at 72° C. for 5 min. The 450 bp PCR product was labeled with [α-32P] dCTP using Multiprime labeling system (Amersham Life Science). The blot was hybridized with the probe using standard technique (Sambrook et al, (1989), above). The specific activity of the probe was $0.8 \times 10^9$ cpm/ug DNA and used at $1 \times 10^6$ cpm/ml. The final wash was in 0.3×SSC, 0.5% SDS at 65° C., and exposed to X-OMAT AR film (Kodak) with an intensifying screen at −70° C.

A blot containing PstI-digested genomic DNA from a human-rodent somatic hybrid cell panel was obtained from Oncor (Gaithersburg, Md.), and probed with the [$^{32}$P]cysteine-rich domain fragment as described above.

Fluorescent In Situ Hybridization—

Metaphase spreads were prepared from phytohaemaglutunin-stimulated peripheral blood lymphocytes of a 46,XY male donor using standard cytogenetic procedures. The fragment 6 was amplified by recombinant PCR with the fragment 3 and 4 (see FIG. 2A). PCR was performed with each of the fragment 3 and 4 and the primers 028 and 019 in the same conditions for the fragment 3 except using longer extension period (7 min) for cycling. The fragment 6 was labelled with biotin-14-dCTP using a BioPrime random prime labelling kit (Bethesda Research Laboratories, Gaithersburg, Md.), and hybridized to metaphase cells on slides. Conditions for hybridization and immunofluorescent detection were essentially as described (Morris et al, (1993) *Human Genetics*, 91, 31-36), except that Cot 1 suppression was not required, slides were washed to a stringency of 0.1×SSC, 60° C. after hybridization, and an additional amplification step was needed because of the small size of the probe. For precise chromosome band localization, DAPI and FITC images were captured separately for each metaphase from the fluorescent microscope to computer using a Photometrics KAF1400 CCD camera and IPLAB Spectrum software (Signal Analytics, VA), and colour-joined using Multiprobe extension software.

Northern Blot Analysis—

Approximately 10 ug of total RNA from cultured cells were fractionated in formaldehyde-denatured 1% agarose gel and transferred to Hybond N+ (Amersham) using 3 M NaCl, 8 mM NaOH, 2 mM sarkosyl with Turboblotter (Schleicher & Schuell, Keene, N.H.) for 3 h. The membrane was UV-crosslinked (Stratalinker, Stratagene), and hybridized with [$^{32}$P]fragment 3 or [$^{32}$P]human §-actin probe using standard techniques (Sambrook et at (1989), above). The specific activity of the probes were $0.9–1.1 \times 10^9$ cpm/ug DNA and used at 0.7–1.1×10⁶ cpm/ml. The final wash was in 0.1×SSC, 0.5% SDS at 68° C., and exposed to X-OMAT AR film (Kodak) with intensifying screen at −70° C.

Reverse Transcription-PCR Analysis—

Total RNA isolated leukocytes was incubated with RNase-free DNaseI (Life Technologies), and was transcribed using Superscriptfl with the oligo dT adaptor primer 018. PCR was performed using a pair of DEC-205 specific primers 060 (GTGGATCCAGTACAAGGGTCA at nucleotide 4655-4686) (SEQ ID NO: 29) and 056 (ACCAAATCAGTCCGC-CCATGA at nucleotide 5116-5096) (SEQ ID NO: 30) with Taq polymerase in the presence of a PCR additive, Q buffer (Qiagen) by touch down PCR (Don, R. H., Cox, P. T., Wainwright, B. J., Baker, K., and Mattick, J. S., (1991) Nucleic Acid Res. 19, 4008). PCR conditions used were the initial denaturation at 92° C. for 2 min, 21 cycles of denaturation at 92° C. for 15 sec, annealing at 60° C. minus 0.5° C./cycle for 15 sec, extension at 68° C. for 30 sec, 15 cycles of denaturation at 92° C., annealing at 50° C., extention at 68° C. for 1 min and the final extension at 68° C. for 5 min. Human glycelaldehyde-3-phosphate dehydrogenase (GAPDH) (Tokunaga, K., Nakamura, Y., Sakata, K., Fujimori, K., Ohkubo, M., Sawada, K., and Sakiyama, S. (1987) Cancer Res. 47, 5616-5619) was used for normalization. The primers for GAPDH were 053 (ATGGGGAAGGTGAAGGTCGGA-3' at nucleotide 61-81) (SEQ ID NO: 31), and 055 (AGGGGCCATCCACAGTCTTCT-3' at nucleotide 634-614) (SEQ ID NO: 32). The PCR reactions were fractionated with 1.5% agarose gel in TAE buffer, and stained with 0.5 ug/ml ethidium bromide.

Sequence Data Analysis—

The National Center of Biotechnology Information (NCBI) Center electronic mail server BLAST was used to search for homologous sequences. Sequence alignments and motif search were done using Bestfit and Motifs programs, respectively, of GCG computer package (Madison, Wis.).

Results

Isolation of cDNA for Human DEC-205.

Based on the amino acid sequence of mouse DEC-205, a set of degenerate primers were synthesized and used to perform RT-PCR using the Hodgkin's disease-derived L428 cell line and the myeloid HEL cell lines (FIG. 2). The two pair of primers (DEC-d/-e, and DEC-a/-b) gave rise to the specific RT-PCR products, fragment 1 (390 bp) and 2 (150 bp), respectively (FIGS. 2A and 2B). These specific fragments were cloned and sequenced (data not shown). The deduced amino acid sequences of fragment 1 and 2 were ~80% identical to that of mouse DEC-205, indicating that these fragments were derived from the cDNA of human DEC-205.

Primers nested within these fragments were synthesized and further RT-PCR and 3'-RACE performed using a L428 cDNA pool reverse transcribed with an oligo dT adapter primer 018. A 3.8 kb RT-PCR product (fragment 3) was obtained using primer 028 and 023 (FIGS. 2A and 2C). A 3.2 kb 3'-RACE product (fragment 4) was obtained using primer 029 and an adaptor primer 019 (FIGS. 2A and 2C). The fragment 3 was cloned and several identical clones were identified by restriction enzyme map analysis (data not shown), and one of which, pb38f1, was fully sequenced: The DNA sequence of the fragment 3 (pB38f1) extending from the middle of cysteine-rich domain to the middle of CRD-8 (FIG. 2A), was 82% identical to the published mouse DEC-205 cDNA sequence. The fragment 4 was cloned and two distinct clones identified by restriction enzyme map analysis. Both clones were partially sequenced and the 3' end DNA sequence of one clone (eg. pb30-3) was found to contain a poly A tail, and with 72% identical to 3'-untranslated region of mouse DEC-205 (data not shown). Therefore, the pb30-3 was sequenced to obtain the DNA sequence of the coding region of DEC-205 plus partial 3'-untranslated region. The resulting DNA sequence for the coding region was ~80% identical to that of mouse DEC-205 spanning from the middle of CRD-8 to the end of cytoplasmic domain (FIG. 2A). The DNA sequences obtained from pb38f1 and pb30-3 overlapped by 320 bp, covering 95% of human DEC-205 coding region.

In order to complete the 5' end of the DEC-205 cDNA sequences a L428 cDNA library was screened by plaque hybridization using ³²P-labeled fragment 3 as a probe. A clone (pBKI4-1) was isolated, and the 1.5 kb insert of this clone was sequenced (FIG. 2A). The sequence was ~80% identical to the mouse sequence and corresponded to the signal peptide, cysteine-rich domain, fibronectin type II domain, CRD-1 and part of the CRD-2. The pBK14-1 contained 51 bp 5'-untranslated region, and overlapped with fragment 3 by ~1.2 kb.

To validate the DNA sequence obtained from the PCR clones, a further RT-PCR fragment (fragment 5) amplified with primers 058 (nested in the cysteine-rich domain) and 050 (located ~130 bp downstream of the stop codon) was prepared (FIG. 2A). The fragment 5 PCR product was sequenced directly using IRD$_{41}$-labeled custom primers without cloning. A total of 10 point mutations, presumably generated because of the low fidelity of thermostable polymerases were found and corrected in the PCR clone-derived DNA sequence. The complete cDNA sequence for human DEC-205 is 5166 bp in size, and encodes for a predicted 198 kDa type I transmembrane protein with 1722 amino acids before post translational modification.

The deduced amino acid sequence of human DEC-205 showed 77% overall identity with the homologous mouse protein (FIG. 3A). All the cysteines, and putative N-glycosylation sites in the extracellular domain of mouse DEC-205, were conserved in the human sequence. In the cytoplasmic domain the putative serine phosphorylation sites by protein kinase C or casein kinase, and a tyrosine, which appears to be important for coated pit-mediated internalization (Ezekowitz, R. A. B., Sastry, K., Bailly, P., and Warner, A. (1990) J. Exp. Med. 172, 1785-1794; and Zvaritch, E., Lambeau, G., and Lazdunski, M. (1996) J. Biol. Chem. 271, 250-257), were also conserved. There was one amino acid deletion within the CRD-5 in human DEC-205. All the extracelluar domains, including the cysteine-rich domain, fibronectin type II domain, and CRD1-10 were 74-87% identical between human and mouse sequences (FIG. 3B), suggesting the importance of these domains for the function of DEC-205. In contrast, the two hydrophobic domains, including the signal peptide and transmembrane domain, showed much lower identity (57% and 52%, respectively (FIG. 3B)) with the mouse protein, confirming the observation that these hydrohobic domains are more variable, and rapidly evolved structures (Von Heijne, G. (1990) J. Membrane Biol. 115, 195-201).

DEC-205 is a Single Copy Gene with Polymorphism—

Figure 4:
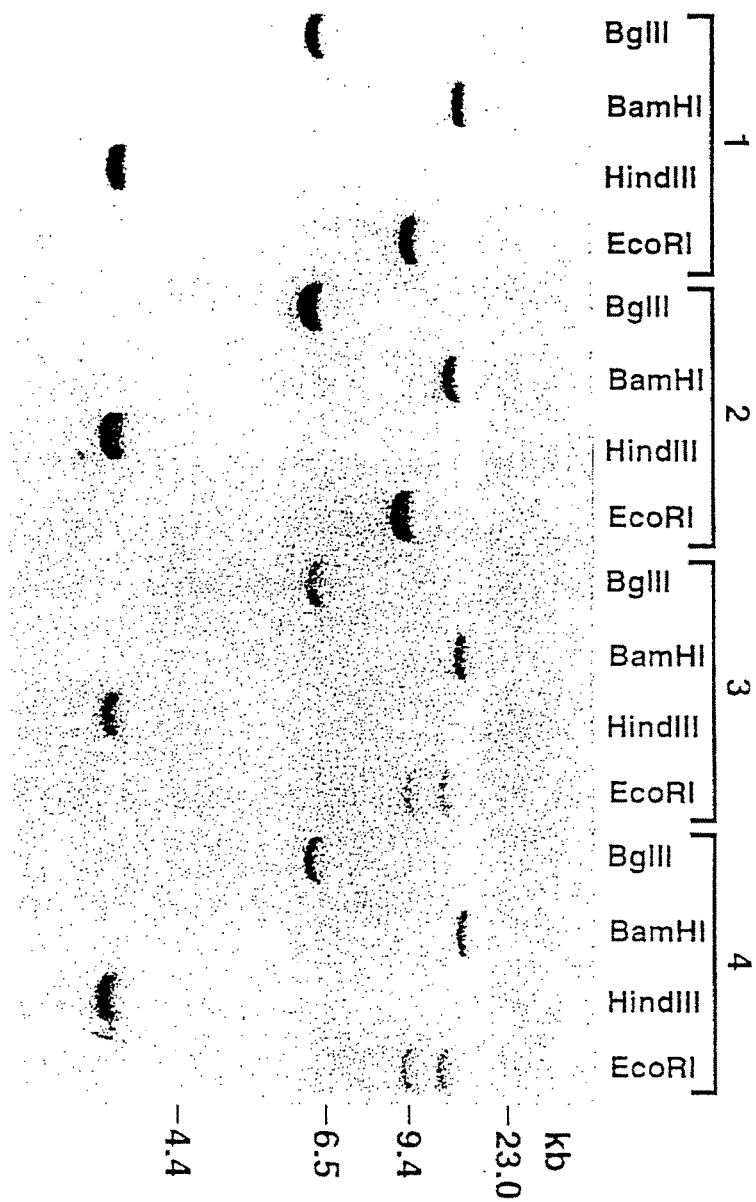
FIG. 4 shows that human DEC-205 is probably a one-copy gene. Genomic DNA isolated from the peripheral blood of four individuals was digested with the restriction enzymes BglII, BamHI, HindIII or EcoRI and subjected to Southern blot analysis with the [$^{32}$P]cysteine-rich domain probe. The final wash was 0.3×SSC at 65° C. The positions of the DNA molecular size standards are indicated to the right.

Peripheral blood-derived genomic DNA from 4 individuals was restriction enzyme-digested with BglII, BamHI, HindIII or EcoRI, and subjected to Southern blot analysis. The cysteine-rich domain of the macrophage mannose receptor (Kim, S. J., Ruiz, N., Bezouska, K., and Drickamer, K. (1992) Genomics 14, 721-727; and Harris, N., Peters, L. L., Eicher, E. M., Rits, M., Raspberry, D., Eichbaum, Q. G., Super, M., and Ezekowitz, R. A. B. (1994) Biochem. Biophys. Res. Com. 198, 682-692) and phospholipase A2 receptor (Ancian, P., Lambeau, G., Mattei, M. G., and Lazdunski, M. (1995) 270, 8963-8970) is encoded by one exon. Therefore, we amplified the cysteine-rich domain of human DEC-205 using primers 058 and 059 as a potential single exon probe (450 bp), and used this to probe the Southern blot in high stringency. A single band appeared in BglII-, BamHI- or HindIII-digested genomic DNA from all individuals, indicating that DEC-205 is a single copy gene (FIG. 4). The EcoRI digests, however, produced a single band in two individuals and double bands in another, indicating that the DEC-205 gene is polymorphic. Further Southern blot analysis with larger panel of individuals showed identical results (data not shown). Therefore, DEC-205 is a single copy gene with at least one polymorphic site.

DEC-205 Gene Maps to Chromosome Band 2q24—

In order to map the human DEC-205 gene, a somatic cell hybrid panel Southern blot (PstI-digested) was probed with the [$^{32}$P]cysteine-rich domain as described above (FIG. 5). A 3.0 kb band in human genomic DNA was found to hybridize strongly, and the identical band appeared in chromosome 2-containing somatic human-mouse hybrid cells, indicating that DEC-205 gene localizes on chromosome 2. The probe also hybridized weakly with hamster DNA, suggesting the presence of DEC-205 homolog in hamster as well as in the mouse (which also hybridized strongly). The origin of the weakly hybridized bands with apparent polymorphism in the human DNA-containing lanes is not known. The identical band appeared in chromosome 2, and may either be related to an alternative exon structure for this region of DEC-205 or result from weak cross hybridization to another gene on chromosome 2.

Figure 6A:
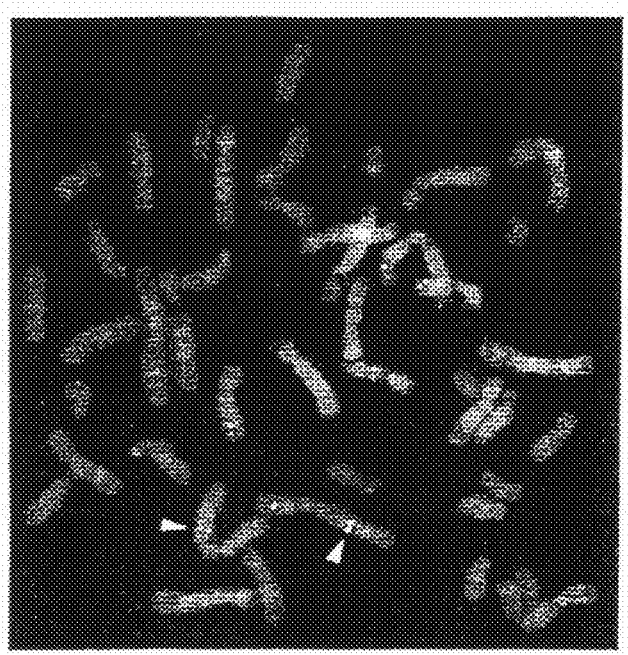
FIG. 6 shows that human DEC-205 gene maps to chromosome band 2q24. A. A metaphase spread of human chromosomes were subjected to fluorescent in situ hybridization (FISH) with 6.6 kb human DEC-205 cDNA probe. The final wash was 0.1×SSC at 60° C. The FISH image was overlaid with a DAPI-stained chromosome image. The DEC-205 specific signals are indicated by the arrowheads. B. An inverted image of chromosome 2 containing DEC-205-specific signal (see FIG. 6A) is aligned with an ideogram of chromosome 2. The chromosome band corresponding to DEC-205 gene is indicated to the right.
Figure 6B:
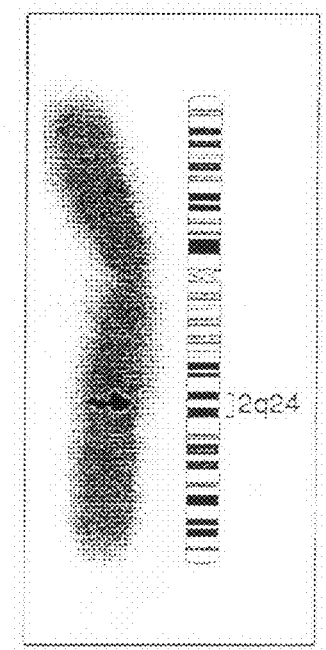

Fluorescent in situ hybridization then was used to map the DEC-205 gene in detail (FIGS. 6A and 6B). The 6.4 kb recombinant PCR fragment (fragment 6) (FIG. 2A) was prepared from fragment 3 and 4, labeled with biotinylated nucleotides, and used as a probe in a high stringency (FIG. 6A). Ninety-one (80%) of a combined total 114 metaphase cells analysed from three experiments showed fluorescent signals on one (27) or both (64) chromosomes 2 in the middle of the long arm, specifically in band q24 (FIG. 6B). High resolution banding analysis provided a more precise location of signals (not shown). No additional site-specific signals were detected on any other chromosome.

DEC-205 Exhibits Multiple Transcripts in Cell Lines—

Figure 7:
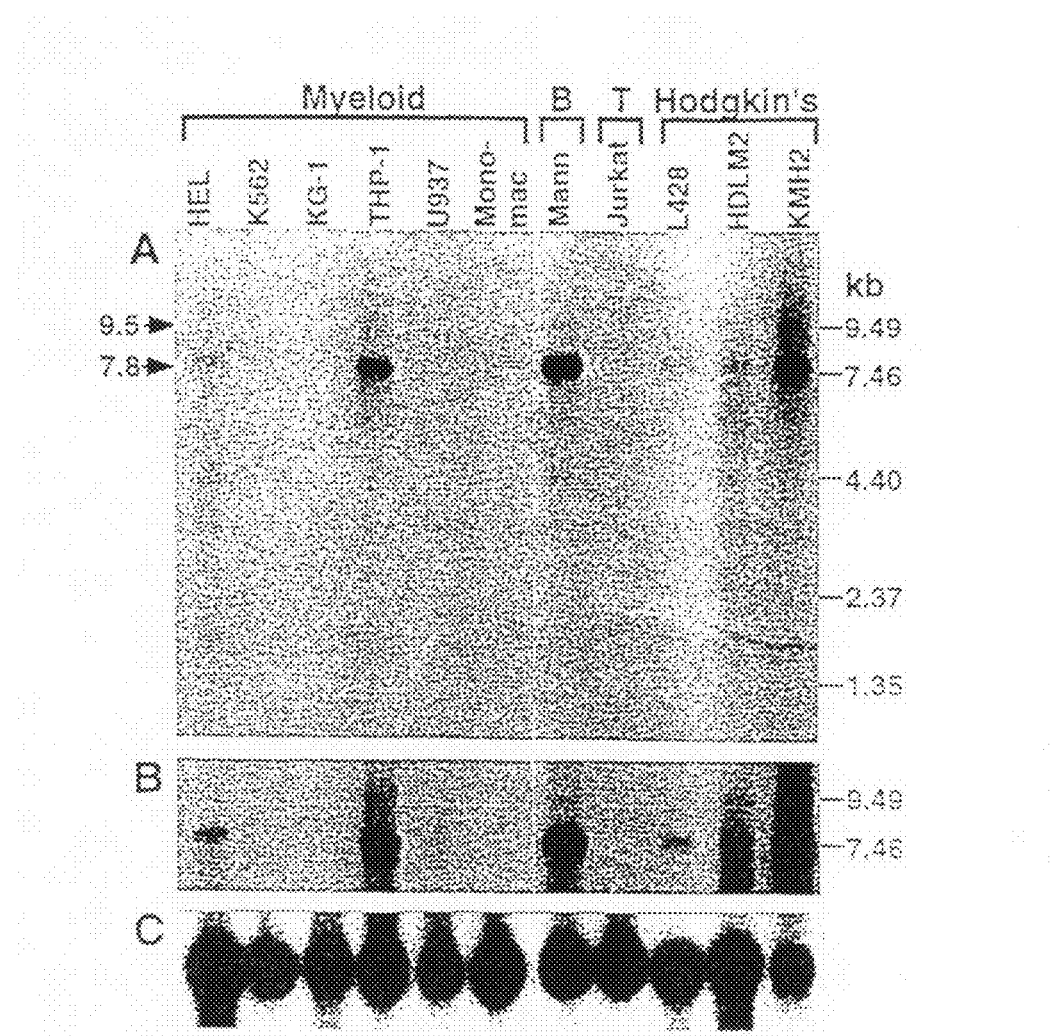
FIG. 7 shows that expression of DEC-205 transcripts within human hematopoetic cell lines. Total RNA prepared from the cell lines were subjected to Northern blot analysis with the [$^{32}$P]fragment 3 (A and B), or [$^{32}$P]-actin (C) probes. The final wash was 0.1×SSC at 65° C. The positions of the RNA molecular size standards are indicated to the right. The estimated molecular size of DEC-205 transcripts are indicated to the left. A, 24 h exposure; B, 72 h exposure.
Figure 8:
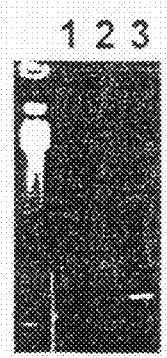
FIG. 8 shows RT-PCR analysis of DEC-205 mRNA in human DC preparations. Specific product is seen using lineage negative; fresh DC (lane 2) and a stronger signal with CMRF-44$^+$ low density cultured DC (lane 3). CD8$^+$ T lymphocytes (lane 1) contain no DEC-205 mRNA Ethidium stain.

A panel of human cell lines, including myeloid, B lymphoid, T lymphoid and Hodgkin's disease-derived cell lines, were analyzed for the expression of DEC-205 transcripts by Northern blot analysis with the [$^{32}$P]fragment 3 as a probe (FIGS. 7A and 7B). Two DEC-205 transcripts, 7.8 and 9.5 kb in size, were detected, and the 7.8 kb transcript was the most abundant. The expression level varied between cell lines, however the myeloid cell line THP-1, the B lymphoid cell line Mann and the Hodgkin's disease cell line KMH2 showed the highest level of expression. Even with longer exposure, DEC-205 transcripts were not detectable in K562, KG-1, Monomac and Jurkat cells, suggesting these cells are DEC—205 negative (FIG. 7B). Interestingly all Hodgkin's disease-derived cell lines tested express the transcripts. Semiquantitative RT-PCR studies also support these results (data not shown).

C. Recombinant Expression of Human DEC-205

In yet another aspect, the present invention relates to the recombinant expression of human DEC-205 or of its extracellular domain.

The Polynucleotides that encode human DEC-205 or the extracellular domain of the invention may be inserted into known vectors for use in standard recombinant DNA techniques. Standard recombinant DNA techniques are those such as are described in Sambrook et al.; "Molecular Cloning" 2nd Edition Cold Spring Harbour Laboratory Press (1987) and by Ausubel et al., Eds, "Current Protocols in Molecular Biology" Greene Publishing Associates and Wiley-Interscience, New York (1987).

Vectors for expressing proteins in bacteria, especially *E. coli* are known. Such vectors include the PATH vectors described by Dieckmann and Tzagoloff in *J. Biol. Chem.* 260, 1513-1520 (1985). These vectors contain DNA sequences that encode anthranilate synthetase (TrpE) followed by a polylinker at the carboxy terminus. Other expression vector systems are based on beta-galactosidase (pGEX); lambda P maltose binding protein (pMAL); and gluthathione S-transferase (pGST)—see *Gene* 67, 31 (1988) and *Peptide Research* 3, 167 (1990).

Vectors useful in yeast and insect cells are available and well known. A suitable example of a yeast vector is the 2µ plasmid.

Suitable vectors for use in mammalian cells are also known. Such vectors include well-known derivatives of SV-40, adenovirus, retrovirus-derived DNA sequences and vectors derived from combination of plasmids and phage DNA.

Further eucaryotic expression vectors are known in the art (e.g. P. J. Southern and P. Berg, *J. Mol. Appl. Genet.* 1, 327-341 (1982); S. Subramani et al, *Mol. Cell. Biol.* 1, 854-864 (1981); R. J. Kaufmann and P. A. Sharp, "Amplification And Expression of Sequences Cotransfected with a Modular Dihydrofolate Reductase Complementary DNA Gene," *J. Mol. Biol.* 159, 601-621 (1982); R. J. Kaufmann and P.A. Sharp, *Mol. Cell. Biol.* 159, 601-664 (1982); S. I. Scahill et al, "Expression And Characterization Of The Product Of A Human Immune Interferon DNA Gene In Chinese Hamster Ovary Cells," *Proc. Natl. Acad. Sci. USA* 80, 4654-4659 (1983); G. Urlaub and L. A. Chasin, *Proc. Natl. Acad. Sci. USA* 77, 4216-4220, (1980).

The expression vectors useful in the present invention contain at least one expression control sequence that is operatively linked to the DNA sequence or fragment to be expressed. The control sequence is inserted in the vector in order to control and to regulate the expression of the cloned DNA sequence. Examples of useful expression control sequences are the lac system, the trp system, the tac system, the trc system, major operator and promoter regions of phage lambda, the control region of fd coat protein, the glycolytic promoters of yeast, e.g. the promoter for 3-phosphoglycerate kinase, the promoters of yeast acid phosphatase, e.g. PhoS, the promoters of the yeast alpha-mating factors, and promoters derived from polyoma, adenovirus, retrovirus, and simian virus, e.g. the early and late promoters or SV40, and other sequences known to control the expression of genes of prokaryotic and eucaryotic cells and their viruses or combinations thereof.

Vectors containing the receptor-encoding DNA and control signals are inserted into a host cell for expression of the receptor. Some useful expression host cells include well-known prokaryotic and eucaryotic cells. Some suitable prokaryotic hosts include, for example, *E. coli*, such as *E. coli* SG-936, *E. coli* HB101, *E. coli* W3110, *E. coli* X1776, *E. coli* X2282, *E. coli* DHT, and *E. coli* MR01, *Pseudomonas, Bacillus*, such as *Bacillus subtilis* and *Streptomyces*. Suitable eucaryotic cells include yeast and other fungi, insect, animal cells, such as COS cells and CHO cells, human cells and plant cells in tissue culture.

D. Ligands

The invention also includes ligands that bind to human DEC-205 of the invention.

The ligand will usually be an antibody or an antibody binding fragment raised against human DEC-205 or its extracellular domain, or against fragments thereof.

Such antibodies may be polyclonal but are preferably monoclonal. Monoclonal antibodies may be produced by methods known in the art. These methods include the immunological method described by Kohler and Milstein in *Nature* 256, 495-497 (1975) and Campbell in "Monoclonal Antibody Technology, the Production and Characterization of Rodent and Human Hybridomas" in Burdon et al. Eds, Laboratory Techniques in Biochemistry and Molecular Biology, Volume 13, Elsevier Science Publishers, Amsterdam (1985); as well as by the recombinant DNA method described by Huse et al. in *Science* 246, 1275-1281 (1989).

In yet another form, the ligand may also be a non-protein, probably carbohydrate containing, molecule that acts as a ligand when it binds to, or otherwise comes into contact with, human DEC-205.

In addition, ligands may be of two functional types. The first functional type of ligand is a molecule which binds to human DEC-205 and stimulates it in performing its normal function (a "stimulant ligand"). The second functional type of ligand is a molecule which binds to human DEC-205 and inhibits or prevents it performing its normal function (an "antagonistic ligand").

Both types of ligand will find application in either therapeutic or prophylactic treatments as described below.

Example 3 describes the production of anti-DEC-205 antibodies.

Example 3

Production of Anti-DEC-205 Antibodies

Figure 9:
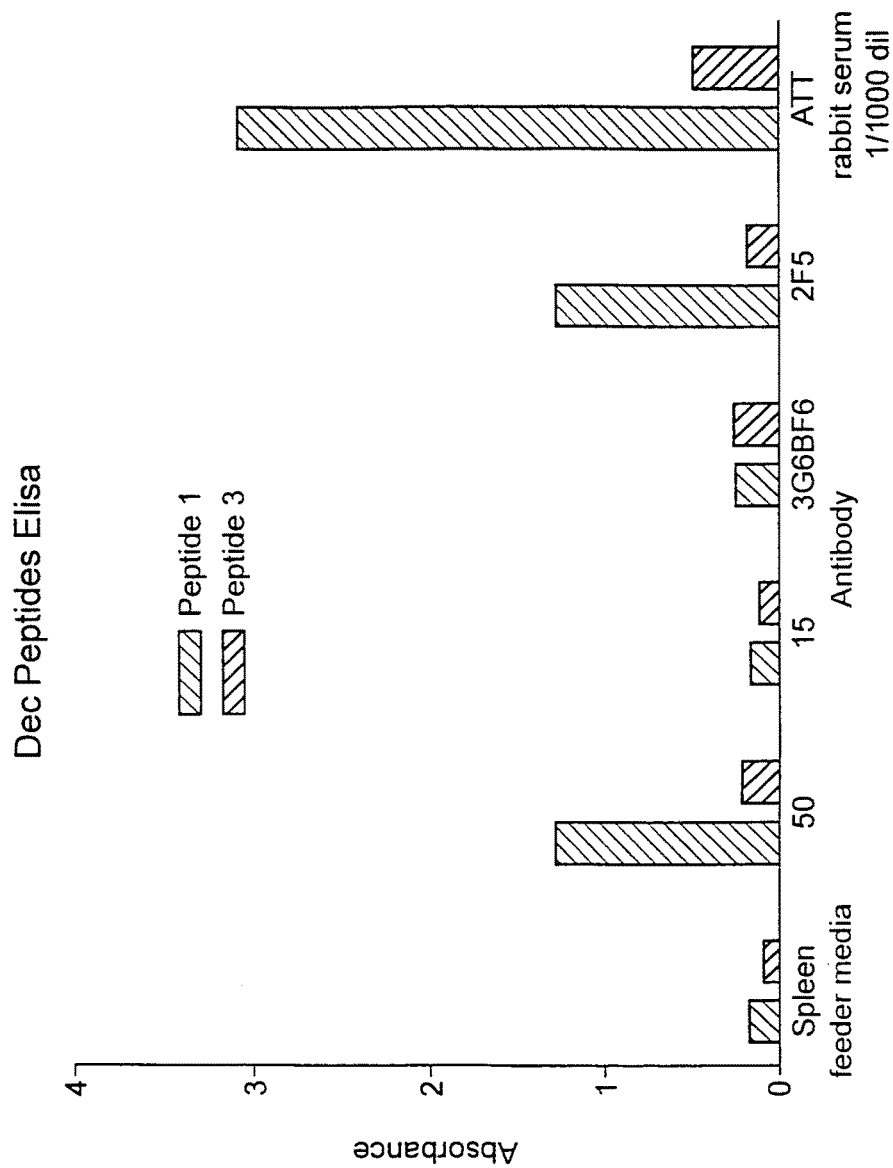
FIG. 9 represents the result of an ELISA assay showing a monoclonal antibody binding specifically to DEC-205 peptide 1 and not peptide 3. Positive control binding of a hyperimmunized rabbit anti-DEC-205-peptide 1 serum and hyperimmunized rabbit anti-DEC-205-peptide 2 serum are shown.

A BALB/c mouse was immunized ip/sc with L428 cells and boosted SC with two peptides derived from the DEC-205 cDNA sequence. DEC-205 peptide 1 ATTQDEVHTKC (SEQ ID NO: 33) (aa1267-aa1277) and DEC-205-peptide 2 TEKEVKPVDSVKC (SEQ ID NO: 34) (aa1227-aa1239) were synthesized by Chiron Mimotopes Pty Ltd (Clayton, Victoria, Australia). After a third immunization with the two DEC-205 peptides sc/ip/IV the mouse was sacrificed and a spleen cell suspension prepared. The spleen cells were fused with the NS-1 myeloma cell line using standard techniques (Hock et al, Immunology 1994; 83:573). A hybridoma was subsequently isolated, 2F5, which produced monoclonal antibody binding to the DEC-205-peptide 1 but not the DEC-205-peptide 2 or a third control DEC-205-peptide 3 (KCLGLDITKSVNELR) (SEQ ID NO: 35) (aa82-aa96). This is shown by FIG. 9.

E. Constructs

The invention also provides constructs. The constructs will generally include antigens against which an immune response is desired but can also include other products to be delivered specifically to dendritic cells. Toxins, such as the ricin A chain are not excluded. The other component of the construct will vary, being either a ligand as described above or at least the extracellular domain of human DEC-205. Both constructs will have the potential to manipulate the immune system of the host.

In the ligand-antigen constructs, ligands which bind to human DEC-205 (usually antibodies, antibody-binding fragments or carbohydrates expressing proteins) can be coupled or otherwise associated with the antigen against which an immune response is desired. An example of such antigens are sugar-coated antigens such as tumour-associated antigens. In use, the ligand component binds to human DEC-205 and the dendritic cell is 'primed' with the associated antigen. This 'priming' action will assist in the induction of an immediate immune response against the antigen.

The ligand-antigen construct can take any appropriate form for administration to the dendritic cells. Such forms may differ depending upon whether the therapeutic protocol involves isolation of the patients dendritic cells (so that the priming action can take place in vitro) or whether the construct is to be administered to a patient in vivo.

The construct can be directly administered to a patient for in vivo treatment. It can also be administered in a form which allows the construct to be expressed within the patient.

One example of such a form for administration to a patient in vivo is a live recombinant viral vaccine. Such a vaccine includes a polynucleotide encoding the DEC-205 ligand (or a portion thereof) and the antigen. The vaccine is administered to the patient and, once within the patient, expresses the encoded ligand and antigen to bind to the patients dendritic cells (via human DEC-205).

A number of such live recombinant viral vaccine systems are known. An example of such a system is the Vaccinia virus system (U.S. Pat. No. 4,603,112; Brochier et al., *Nature* 354: 520 (1991)).

Administration can be via intravenous, intramuscular, subcutaneous, topical, oral, intra nasal, rectal or intracerebroventricular routes, as appropriate.

F. Applications

Human DEC-205, its ligands and the constructs discussed above can be employed therapeutically or prophylactically in accordance with this invention to promote or inhibit any of the known actions of dendritic cells and/or to manipulate the immune system.

Thus, the antagonistic ligands per se have potential application inter alia blocking or inhibiting the immune response during transplantation procedures.

Ligands also have application in delivering other products with which they are associated directly to dendritic cells. This can be for therapeutic purposes (where the delivered product is an immunogenic antigen) as discussed above. It can also be to target a toxin (such as the ricin A-chain specifically to dendritic cells to selectively destroy them as part of an immunosuppressive process.

G. The Use of Human DEC-205 to Detect Dendritic Cells in Cell Suspensions on Tissues and to Purify Dendritic Cells Monoclonal antibodies or other ligands binding to DEC-205 may be used to identify or isolate DC for scientific study or therapeutic application. For this application, the antibodies or ligands can be used in conjunction with conventional identification/separation systems. An example of such a system is the avidin-biotin immunoaffinity system available from CellPro Inc, Washington, USA (see U.S. Pat. No. 5,215,927, U.S. Pat. No. 5,225,353, U.S. Pat. No. 5,262,334 and U.S. Pat. No. 5,240,856).

This system employs directly or indirectly a biotinylated monoclonal antibody directed against a target cell and a column containing immunobilized avidin and can be readily adapted to extract activated human dendritic cells, in this case from human peripheral blood, using the anti-DEC-205 antibody as follows:

1. A sample of human peripheral blood containing the human dendritic cells is mixed with biotinylated anti-DEC-205 antibody and incubated to allow formation of antibody/human DC complexes.
2. Following incubation, the mixture is introduced into a CellPro continuous-flow immunoadsorption column filled with avidin-coated beads, the strong affinity between biotin and avidin causing the biotin-coated antibodies (together with the human DC to which they have bound) to adhere to the avidin-coated beads.
3. After unwanted cells present in the mixture are washed away, captured activated human DC are removed from the column by gentle agitation and are available for use.

Variations on this theme using the anti-DEC-205 antibody as primary antibody (to bind to activated DC) and a biotinylated secondary antibody (to bind to the anti-DEC-205 antibody) can also be employed.

It will be appreciated that before admixture with the anti-DEC-205 antibody in accordance with the above protocol, the human peripheral blood sample should be treated to ensure that the DC the sample contains are activated. This can easily be achieved by, for example, overnight incubation of the sample.

H. Functional Equivalents

The invention includes functional equivalents of human DEC-205, extracellular domains and nucleic acid molecules described above.

Human DEC-205 and its extracellular domain are or include proteins. A protein is considered a functional equivalent of another protein for a specific function if the equivalent protein is immunologically cross-reactive with, and has the same function as, the original protein. The equivalent may, for example, be a fragment of the protein, or a substitution, addition or deletion mutant of the protein.

For example, it is possible to substitute amino acids in a sequence with equivalent amino acids using conventional techniques. Groups of amino acids known normally to be equivalent are:
(a) Ala(A) Ser(S) Thr(T) Pro(P) Gly(G);
(b) Asn(N) Asp(D) Glu(E) Gln(Q);
(c) His(H) Arg(R) Lys(K);
(d) Met(M) Leu(L) Ile(I) Val(V); and
(e) Phe(F) Tyr(Y) Trp(W).

Substitutions, additions and/or deletions in human DEC-205 may be made as long as the resulting equivalent protein is immunologically cross-reactive with, and have the same function as, the native human DEC-205.

The equivalent human DEC-205 will normally have substantially the same amino acid sequence as the native human DEC-205. An amino acid sequence that is substantially the same as another sequence, but that differs from the other sequence by means of one or more substitutions, additions and/or deletions is considered to be an equivalent sequence. Preferably, less than 25%, more preferably less than 10%, and most preferably less than 5% of the number of amino acid residues in the amino acid sequence of the native human DEC-205 are substituted for, added to, or deleted from.

Equivalent nucleic acid molecules include nucleic acid sequences that encode proteins equivalent to human DEC-205 as defined above. Equivalent nucleic acid molecules also include nucleic acid sequences that, due to the degeneracy of the nucleic acid code, differ from native nucleic acid sequences in ways that do not affect the corresponding amino acid sequences.

Those persons skilled in the art will of course appreciate that the above description is provided by way of example only and that the invention is limited only by the lawful scope of the appended claims.

The invention claimed is:

1. An isolated monoclonal antibody that specifically binds to human DEC-205 which has the amino acid sequence set forth in SEQ ID NO: 1, wherein the monoclonal antibody specifically binds the amino acid sequence of SEQ ID NO: 33 (ATTQDEVHTKC).

2. An antigen binding fragment of the antibody as claimed in claim 1.

* * * * *